(12) United States Patent
Boiangiu et al.

(10) Patent No.: US 8,398,714 B2
(45) Date of Patent: Mar. 19, 2013

(54) DENTAL BONE IMPLANT, METHODS FOR IMPLANTING THE DENTAL BONE IMPLANT AND METHODS AND SYSTEMS FOR MANUFACTURING DENTAL BONE IMPLANTS

(75) Inventors: Andy Boiangiu, Holon (IL); Yossi Haran, Modiln (IL)

(73) Assignee: Andy Boiangiu, Holon (IL)

( * ) Notice: Subject to any disclaimer, the term of this patent is extended or adjusted under 35 U.S.C. 154(b) by 0 days.

(21) Appl. No.: 13/060,449

(22) PCT Filed: Aug. 26, 2009

(86) PCT No.: PCT/IL2009/000826
§ 371 (c)(1),
(2), (4) Date: Feb. 24, 2011

(87) PCT Pub. No.: WO2010/023665
PCT Pub. Date: Mar. 4, 2010

(65) Prior Publication Data
US 2011/0151400 A1      Jun. 23, 2011

Related U.S. Application Data

(60) Provisional application No. 61/136,299, filed on Aug. 26, 2008.

(51) Int. Cl.
*A61F 2/02* (2006.01)
(52) U.S. Cl. ............... 623/17.17; 623/17.18; 623/16.11
(58) Field of Classification Search ............... 623/16.11, 623/17.17, 17.18; 433/76
See application file for complete search history.

(56) References Cited

U.S. PATENT DOCUMENTS

| | | | |
|---|---|---|---|
| 4,787,906 A | 11/1988 | Haris | |
| 6,645,250 B2 * | 11/2003 | Schulter | 623/17.17 |
| 8,052,423 B2 * | 11/2011 | Ali Alghamdi | 433/215 |
| 2005/0273165 A1 * | 12/2005 | Griffiths et al. | 623/16.11 |
| 2009/0036889 A1 * | 2/2009 | Callender | 606/55 |
| 2012/0100500 A1 * | 4/2012 | Gao | 433/72 |

FOREIGN PATENT DOCUMENTS

| | | |
|---|---|---|
| DE | 102006047054 | 4/2008 |
| EP | 0107476 | 5/1984 |
| WO | WO 2010/023665 | 3/2010 |

OTHER PUBLICATIONS

Communication Relating to the Results of the Partial International Search Dated Feb. 10, 2010 From the International Searching Authority Re.: Application No. PCT/IL2009/000826.
International Search Report and the Written Opinion Dated May 3, 2010 From the International Searching Authority Re.: Application No. PCT/IL2009/000826.
International Preliminary Report on Patentability Dated Mar. 10, 2011 From the International Bureau of WIPO Re.: Application No. PCT/IL2009/000826.

* cited by examiner

*Primary Examiner* — Thomas J Sweet
*Assistant Examiner* — Seema Mathew
(74) *Attorney, Agent, or Firm* — Simon Kahn; Chanoch Kahn

(57) ABSTRACT

A dental bone implant that comprises a first fitted bone graft sized and shaped to fit tightly to a buccal surface of a periodontal alveolar bone around at least one tooth and to reconstruct at least a portion of one or more periodontal bone defect and a second fitted bone graft sized and shaped to fit tightly to a lingual/palatal surface of a periodontal alveolar bone around at least one tooth and to reconstruct at least an additional portion of at least one periodontal bone defect. The portion and the other portion complementary cover the one or more periodontal bone defects.

15 Claims, 27 Drawing Sheets

DENTAL BONE IMPLANT, METHODS FOR IMPLANTING THE DENTAL BONE IMPLANT AND METHODS AND SYSTEMS FOR MANUFACTURING DENTAL BONE IMPLANTS

RELATED APPLICATIONS

This application is a National Phase of PCT Patent Application No. PCT/IL2009/000826 having International filing date of Aug. 26, 2009, which claims the benefit of priority of U.S. Provisional Patent Application No. 61/136,299, filed on Aug. 26, 2008. The contents of the above applications are all incorporated herein by reference.

FIELD AND BACKGROUND OF THE INVENTION

The present invention, in some embodiments thereof, relates to dental bone implants and, more particularly, but not exclusively, to dental bone implants and to the production and/or implantation thereof.

Periodontal disease occurs when bacteria colonize the sulcus space between the teeth and gingiva. The bacteria cause inflammation which destroys the gingival epithelial lining and epithelial attachment to the tooth. The inflammation then progresses down the tooth root towards the apex of the root and destroys periodontal structure and bone. As periodontal disease progresses open pockets develop between the tooth and the gingiva. A dentist can determine the presence and extent of periodontal disease using a probe to measure the depth of pockets between each tooth and gingiva. X-rays can reveal the extent of any bone loss.

A common surgical procedure has been widely used to treat bone loss caused by periodontal disease. In this procedure the periodontist uses a scalpel to incise the gingiva and reflects it back to expose the tooth root and bone. Then he removes the irregular shaped bone with hand instruments or rotary instruments, surgically removes granulation tissue and gingiva, cleans the site and places a bone regeneration material into osseous periodontal bone defects that remain in the bone. Guided Tissue Regeneration barriers are placed over bone regeneration material in deeper osseous periodontal bone defects. He then sutures the gingiva around the tooth. The gingiva, epithelial attachment, bone, and periodontal ligament between the tooth and bone then form themselves again.

Various methods and systems have been developed to supporting the process of bone regeneration. Fir example, US Publication No. 2008/0090208 to Rubbert teaches a CAD/CAM system for customized dental prosthesis for periodontal or osseointegration, wherein a CAD/CAM system is used to customize implants for a patient. Another example is described in U.S. Pat. No. 7,105,812 to Szymaitis that teaches a compositing for inducing periodontal regeneration using a composition that is injected into a targeted periodontal space to induce regeneration of bone in the degenerated periodontal region.

SUMMARY OF THE INVENTION

According to some embodiments of the present invention there is provided a dental bone implant. The dental bone implant comprises a first fitted bone graft sized and shaped to fit tightly to a buccal surface of a periodontal alveolar bone around at least one tooth and to reconstruct at least a portion of at least one periodontal bone defect and a second fitted bone graft sized and shaped to fit tightly to a lingual/palatal surface of a periodontal alveolar bone around at least one tooth and to reconstruct at least an additional portion of at least one periodontal bone defect. The portion and the portion complementary cover the at least one periodontal bone.

Optionally, the first fitted bone graft having a first extension sized and shaped to reconstruct completely a first tooth socket and the second fitted bone graft having a second extension sized and shaped to reconstruct completely a second tooth socket.

More optionally, the first and second tooth socket are placed on different sides of a common tooth of the at least one tooth.

More optionally, at least one of the first and second extensions having at least one foundation element for a dental implant.

Optionally, at least one of the first and second fitted bone grafts is configured to be implanted on top of the periodontal alveolar bone until being entirely replaced by native bone originated from a growth of the periodontal alveolar bone.

Optionally, the at least one tooth comprises a plurality of teeth, wherein at least one of the first and second fitted bone grafts being sized and shaped to fit tightly to an interdental surface between the plurality of teeth.

Optionally, at least one of the first and second fitted bone grafts having a structure defined by a three dimensional model of the periodontal alveolar bone.

Optionally, at least one of the first and second fitted bone grafts is at least partly coated with at least one of a barrier membrane and a gingival tissue growth promoting membrane.

Optionally, at least one of the first and second fitted bone grafts having at least one surgical guidance element indicative of at least one of a drilling location for anchoring the fitted bone graft and a drilling location for adding a dental implant.

Optionally, at least one of the first and second fitted bone grafts having at least one foundation element for supporting at least one dental implant.

Optionally, at least one of the first and second fitted bone grafts is sized and shaped to reconstruct at least one teeth socket.

Optionally, at least one of the first and second fitted bone grafts comprises a periodontal regenerative agent.

More optionally, the periodontal regenerative agent is selected from a group consisting of promoting regeneration agent and limiting regeneration agent.

Optionally, at least one of the first and second fitted bone grafts is shaped for vertical augmentation.

According to some embodiments of the present invention there is provided a dental bone implant. The dental bone implant comprises a fitted bone graft sized and shaped to fit tightly to at least one of buccal and lingual/palatal surfaces of a periodontal alveolar bone around at least one tooth and to reconstruct at least a portion of at least one periodontal bone defect. The fitted bone graft is configured to be anchored between the periodontal alveolar bone and a gingival tissue of a patient for a period of at least one week.

Optionally, the dental bone implant comprises an additional fitted bone graft sized and shaped to fit closely to another of the buccal and lingual/palatal surfaces around the at least one tooth and to reconstruct another portion of at least one periodontal bone defect.

More optionally, the portion and the another portion complementary cover the at least one periodontal bone.

Optionally, the fitted bone graft having an extension sized and shaped to reconstruct completely at least one tooth socket in proximity to the at least one tooth.

More optionally, the extension having at least one foundation element for a dental implant.

According to some embodiments of the present invention there is provided a dental bone implant. The dental bone implant comprises a fitted bone graft sized and shaped to fit tightly to a surface of a periodontal alveolar bone and to reconstruct at least a portion of at least one periodontal bone defect and at least one surgical guide element each indicative of at least one of a placement of a tooth implant on the fitted bone graft and a drilling location for anchoring the fitted bone graft to the periodontal alveolar bone. The fitted bone graft is configured to be implanted between the surface and a gingival tissue of a patient for a period of at least one week.

According to some embodiments of the present invention there is provided a dental bone implant. The dental bone implant comprises at least one bone graft sized and shaped to reconstruct at least one periodontal bone defect and to fit tightly to an edentulous surface of a periodontal alveolar bone, the at least one bone graft having a plurality of foundation elements for at least one dental implant. The at least one bone graft is configured to be implanted between the surface and a gingival tissue of a patient for a period of at least one week.

Optionally, the at least one bone graft is configured to be implanted on top of the periodontal alveolar bone until being entirely replaced by native bone originated from a growth of the periodontal alveolar bone.

According to some embodiments of the present invention there is provided a method for providing a dental bone implant model. The method comprises receiving imaging data depicting at least one jaw-bone of a patient, creating a three dimensional (3D) model of the at least one jaw-bone according to the imaging data, providing a reference model of the at least one jaw-bone, computing a dental bone implant model based one a space between the 3D model and the reference model, and outputting the dental bone implant model so as to allow the generation of at least one fitted bone graft for reconstructing of at least one periodontal bone defect in the at least one jaw-bone.

Optionally, the creating comprises splitting the 3D model to a plurality of sub models each defining a structure of a bone graft sized and shaped to fit tightly to a portion of the at least one periodontal bone defect on one of buccal and lingual/palatal sides of one of the at least one jaw-bone.

Optionally, the computing comprises registering the reference model according to the 3D model before evaluating the space.

Optionally, the computing subtracting the 3D model from the reference model to acquire the space.

Optionally, the imaging data being acquired by a member of a group consisting of a micro laser optical device, a computerized tomography (CT) modality, an intra-oral camera, or an ultrasound modality, a magnetic resonance imager (MRI) modality, an MRI-CT (MRT) modality, a cone beam CT (CBCT) modality, and a confocal scanning modality.

Optionally, the providing comprises selecting the reference model from a repository according to a demographic data pertaining to the patient.

According to some embodiments of the present invention there is provided a method for producing a dental bone implant. The method comprises receiving at least one three dimensional (3D) model each having a surface shaped according to at least one of a lingual/palatal surface and a buccal surface of a periodontal alveolar bone of at least one of jaw-bone of a patient, automatically shaping a bone graft to fit tightly to the at least one of the lingual/palatal surface and the buccal surface according to the 3D model, and providing the bone graft for reconstructing the periodontal alveolar bone.

Optionally, the shaping comprises shaping a mold having a structure defined according to the at least one of the lingual/palatal surface and the buccal surface according to the at least one 3D model and using the mold for shaping the bone graft from at least one of an osteogenetic liquid, an osteogenetic powder, an osteogenetic gel, and a semi solid osteogenetic raw material.

Optionally, the shaping comprises curving a mill blank block according to the at least one 3D model.

Optionally, the automatically shaping comprises smoothing the bone graft.

According to some embodiments of the present invention there is provided a method for implanting a dental implant. The method comprises receiving at least one bone graft sized and shaped to reconstruct at least one periodontal bone defect of a periodontal alveolar bone, separating a gingival tissue from the at least one periodontal bone defect, placing the at least one bone graft to cover tightly the at least one periodontal bone defect, anchoring the at least one bone graft to the periodontal alveolar bone according to at least one surgical guide element on the at least one bone graft, and reattaching the gingival tissue above the at least one bone graft.

Optionally, the method further comprises adding at least one dental implant to the at least one bone graft according to the at least one surgical guide element.

Optionally, the placing further comprises placing at least one of a barrier membrane and a gingival tissue growth promoting membrane between the gingival tissue and the at least one periodontal bone.

Optionally, after the placing the at least one bone graft is placed less then 0.5 mm from the surface of the periodontal alveolar bone in the at least one periodontal bone defect.

According to some embodiments of the present invention there is provided a method for implanting a dental implant. The method comprises receiving at least one fitted bone graft sized and shaped to fit tightly to a surface of a periodontal alveolar bone around at least one tooth and to reconstruct at least a portion of at least one periodontal bone defect, separating a gingival tissue around the at least one tooth from the periodontal alveolar bone, placing the at least one fitted bone graft between the gingival tissue and the periodontal alveolar bone so as to allows the at least one fitted bone graft to substantially encircle the at least one tooth, anchoring the at least one fitted bone graft to the periodontal alveolar bone, and reattaching the gingival tissue above the at least one fitted bone graft.

Optionally, the receiving comprises receiving a plurality of bone grafts each sized and shaped to reconstruct a plurality of portions of the at least one periodontal bone defect, the plurality of portion comprises a first portion on a buccal surface of the periodontal alveolar bone and a second portion on a lingual/palatal surface of the periodontal alveolar bone, the placing comprises placing a different of the plurality of bone grafts on the first portion and another of on the second portion, the anchoring comprising anchoring the plurality of bone grafts, the reattaching comprising reattaching the gingival tissue above the plurality of bone grafts.

Optionally, the fitted bone graft is place as a scaffold for bone tissue regenerating around the at least one tooth.

Optionally, the fitted bone graft is place so as to support the at least one tooth.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
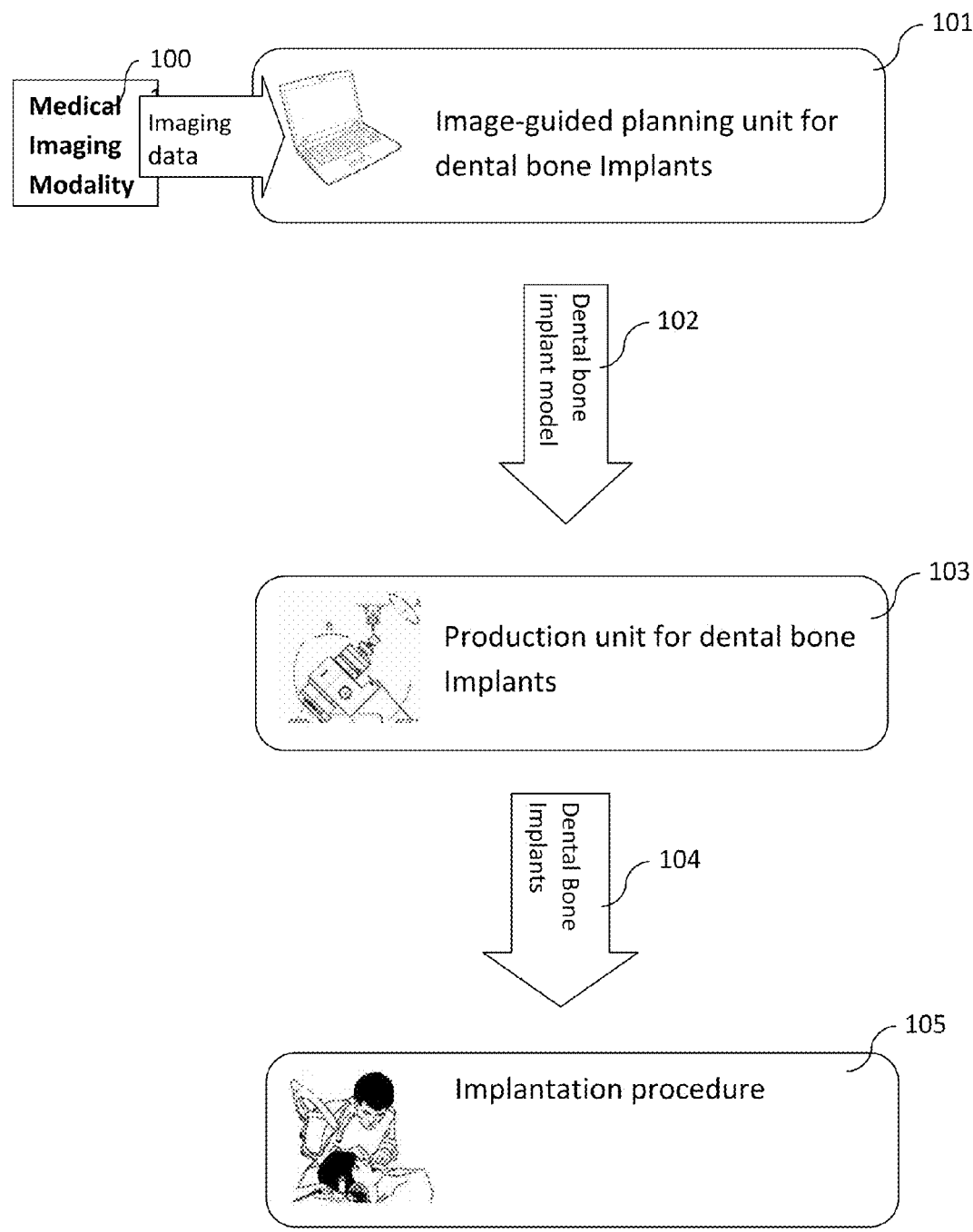
FIG. 1 is a flowchart depicting systems and functionaries involved in a process of reconstructing periodontal bone defects in the mandible and/or the maxilla of a patient using fitted bone grafts, according to some embodiments of the present invention.

The present invention, in some embodiments thereof, relates to dental bone implants and, more particularly, but not exclusively, to dental bone implants and to the production and/or implantation thereof.

According to some embodiments of the present invention there is provided a dental bone implant having one or more bone grafts which are sized and shaped to fit tightly to a surface of a periodontal alveolar bone around one or more teeth. The anchoring of the dental bone implant to the mandible and/or the maxilla provides a scaffold for bone regeneration around the one or more teeth and/or supports the one or more teeth. Optionally, one or more of the bone grafts includes one or more extensions which are sized and shape to fit tightly to the interdental surface. In such a manner, the bone graft may be used for supporting dental implants, such as tooth implants, in proximity to the one or more teeth.

According to some embodiments of the present invention there is provided a pair of complementary bone grafts. In such an embodiment, one of the bone grafts is sized and shaped to fit tightly to a buccal surface portion of one or more periodontal bone defects around one or more teeth in the mandible or the maxilla and the other bone graft is sized and shaped to fit tightly to a lingual/palatal surface portion of the periodontal bone defects. In such an embodiment, the complementary bone grafts may jointly cover buccal, lingual/palatal, and/or interdental surfaces of the mandible or the maxilla without having to extract the one or more teeth. Optionally, one or the bone graft may be anchored, at least partly, to the other bone graft.

According to some embodiments of the present invention there is provided a bone graft having one or more surgical guide elements, markings, foundation elements such as recesses and bores, and/or any surgical indication. Such a bone graft may be implanted according to the one or more surgical guide elements, without using external guidance. The surgical guide elements are optionally added during the production of the bone graft and may according to the structure of the bone graft and/or one or more characteristics of the patient. Optionally, the bone graft is sized and shaped to fit tightly to an edentulate periodontal surface. In such an embodiment, the bone graft may be used to support a number of dental implants so as to allow reconstructing of one or more teeth, optionally all the teeth of a certain jaw-bone.

According to some embodiments of the present invention there is provided a method for generating a 3D model for dental bone implant. The method is based on analyzing imaging data of one or more jaw-bones of a patient so as to allow the creation of a three dimensional (3D) model of the one or more jaw-bones. The model defines the buccal, lingual/palatal, and/or interdental surfaces of the jaw-bones, optionally in a treated area that includes periodontal bone defects. The method is further based on a reference model of the one or more jaw-bones. The dental bone implant model is computed by calculating a space between the 3D model and the reference model. Optionally, the space is computed by subtracting the 3D model, which may be referred to as a patient jaws model, from the reference model. The space defines a structure that fits tightly the buccal, lingual/palatal, and/or interdental surfaces which are defined in the 3D model. Optionally, the structure, referred to herein as a dental bone implant model, may be split to a number of sub model, each defining a different bone graft which his shaped to fit another portion of the buccal, lingual/palatal, and/or interdental surfaces. Now, the structure may be outputted, for example forwarded, to manufacturing unit. The manufacturing unit may produce the dental bone implant according to the received structure.

According to some embodiments of the present invention there is provided a method for manufacturing a dental bone implant according to one or more 3D models and/or sub models. The method is based on one or more 3D models and/or sub models each defines a surface shaped according to a lingual/palatal surface and/or a buccal surface of a periodontal alveolar bone of the mandible and/or the maxilla of a patient. The models allow shaping one or more bone grafts to fit tightly to the surfaces according to the 3D model. The bone graft may be shaped from a designated block, such as a mill blank, and/or using a mold that is shaped according to the received model and/or sub models.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a flowchart depicting units which are involved in a process for reconstructing periodontal bone defects using fitted bone graft, according to some embodiments of the present invention. The process is based on planning, generating and implanting a dental bone implant having bone grafted adjusted according to the surface of the mandible and/or the maxilla of a patient, which may be referred to as jaw-bones, according to some embodiments of the present invention.

Optionally, the produced bone grafts are shaped to tightly fit the surface of the treated area and/or to the one or more teeth in proximity and/or in the treated area. For example, in use, the bone grafts are placed in a manner that the distance between their surface and the surface of the treated area and/or the surface of the one or more teeth is less than 2 mm, 1 mm, for example 0.5 mm, 0.4 mm, 0.3 mm, 0.2 mm, 0.1 mm and/or any intermediate or shorter distance. Optionally, each bone graft is tightly fitted to be placed in proximity to a plurality of teeth, optionally 2, 3, 4, 5, 6, 7, 8, 10, 11, 12, 13, 14, 15 and 16 teeth, optionally less than 1 mm from the surface of each tooth, as described above. It should be noted that such a tight proximity to the periodontal alveolar bone accelerates the osteoconduction, osteoinduction and/or osteogenesis in and around the treated area on which the bone graft is placed. Optionally, the bone graft serves as a tooth scaffold to one or more teeth in the treated area, optionally for a period of at least one week, month, year, and/or as long as the one or more teeth are not extracted or otherwise removed. Optionally, the bone graft serves as a scaffold for bone augmentation, such as vertical bone augmentation and horizontal bone augmentation, which allows reconstructing one or more periodontal bone defects, optionally around one or more teeth in the treated area. Optionally, the bone graft serves as a permanent tooth support to the one or more teeth in the treated area. For clarity, the fitted bone graft that is an element having a rigidity coefficient that is identical or proximate to the rigidity coefficient of a bone. This rigidity coefficient is given ex vivo, before the implantation of the bone graft.

Figure 9A:
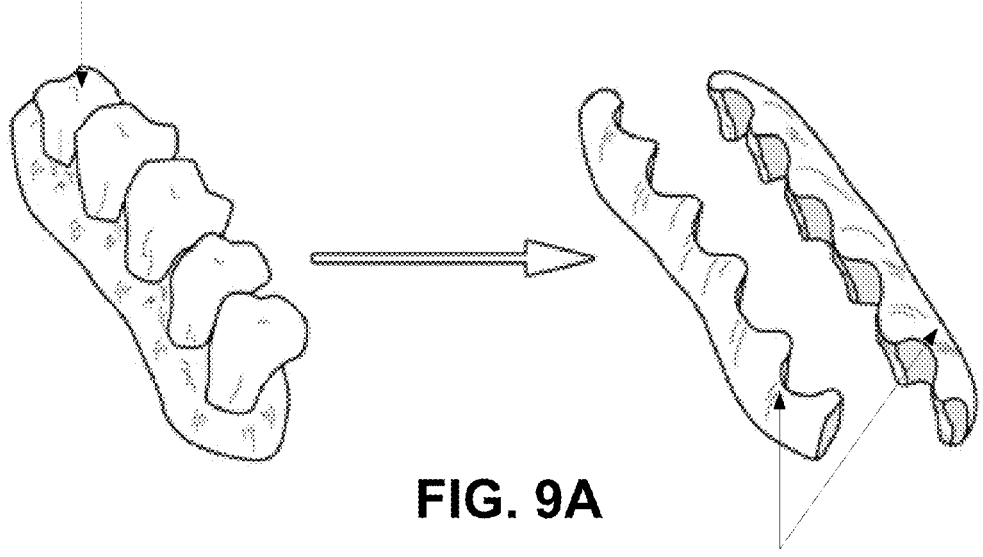
FIGS. 9A-9C are schematic illustrations of exemplary row of teeth and a pair of fitted bone grafts which are respectively fitted thereto, according to some embodiment of the present invention.
Figure 9B:
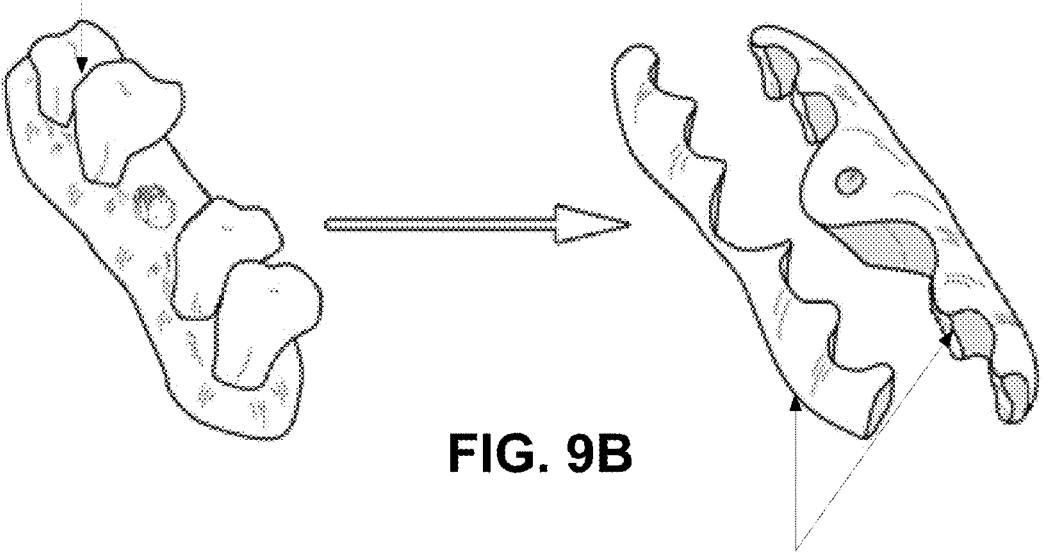

According to some embodiments of the present invention, a dental bone implant having a pair of complementary bone grafts is provided, for example as depicted in FIGS. 9A-9B. In such an embodiment, one of the bone grafts is sized and shaped to fit tightly to a buccal surface portion of one or more periodontal bone defects in the mandible or the maxilla and the other bone graft is sized and shaped to fit tightly to a lingual//palatal surface portion of the one or more periodontal bone defects. Optionally, the lingual/palatal surface portion and the buccal surface portion cover completely, or substantially completely, the surface of one or more periodontal bone defects. Therefore, the complementary bone grafts may be used jointly to reconstruct the one or more periodontal bone defects in the buccal, lingual/palatal, and/or interdental surfaces of the treated area.

Figure 9C:
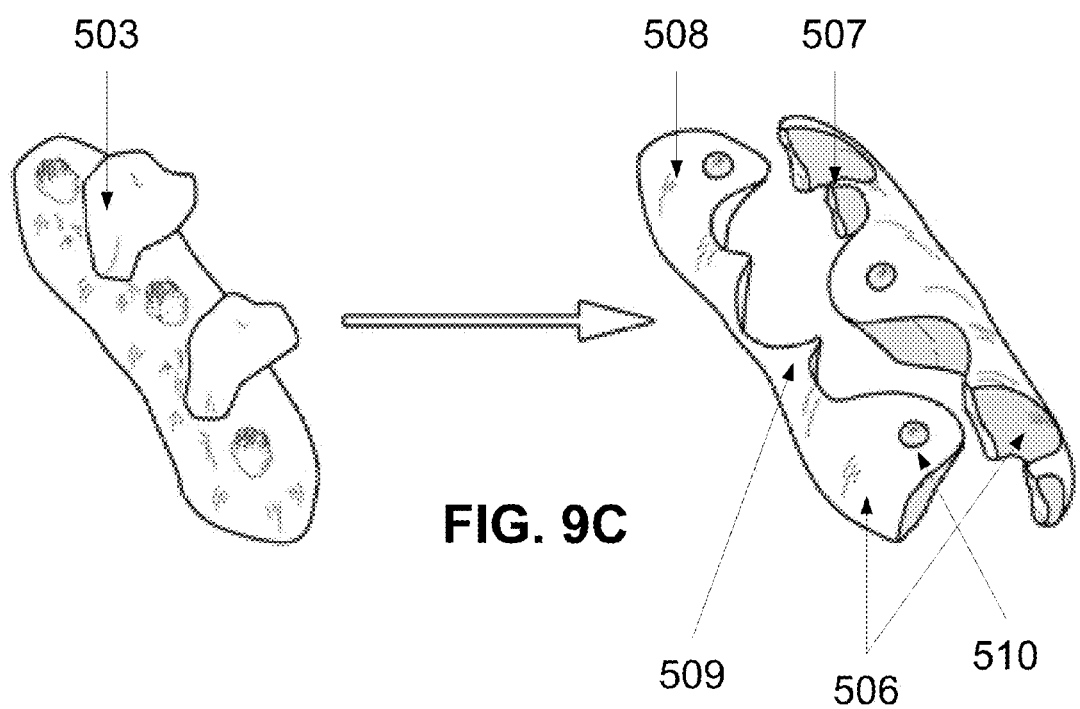
Figure 9D:
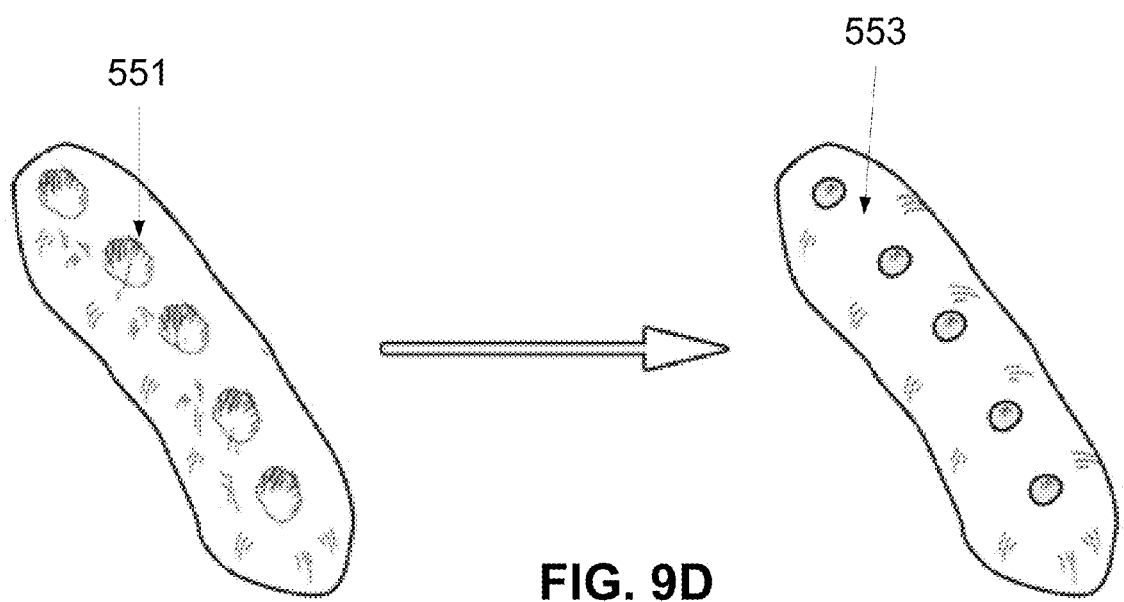
FIGS. 9D-9E are schematic illustrations of exemplary edentulous jaws surfaces and respective fitted bone grafts which are fitted to restore all the teeth sockets, according to some embodiment of the present invention.
Figure 9E:
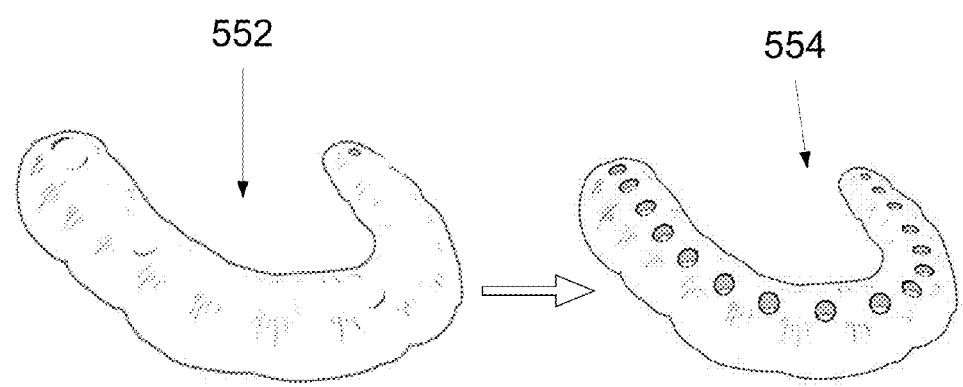
Figure 9F:
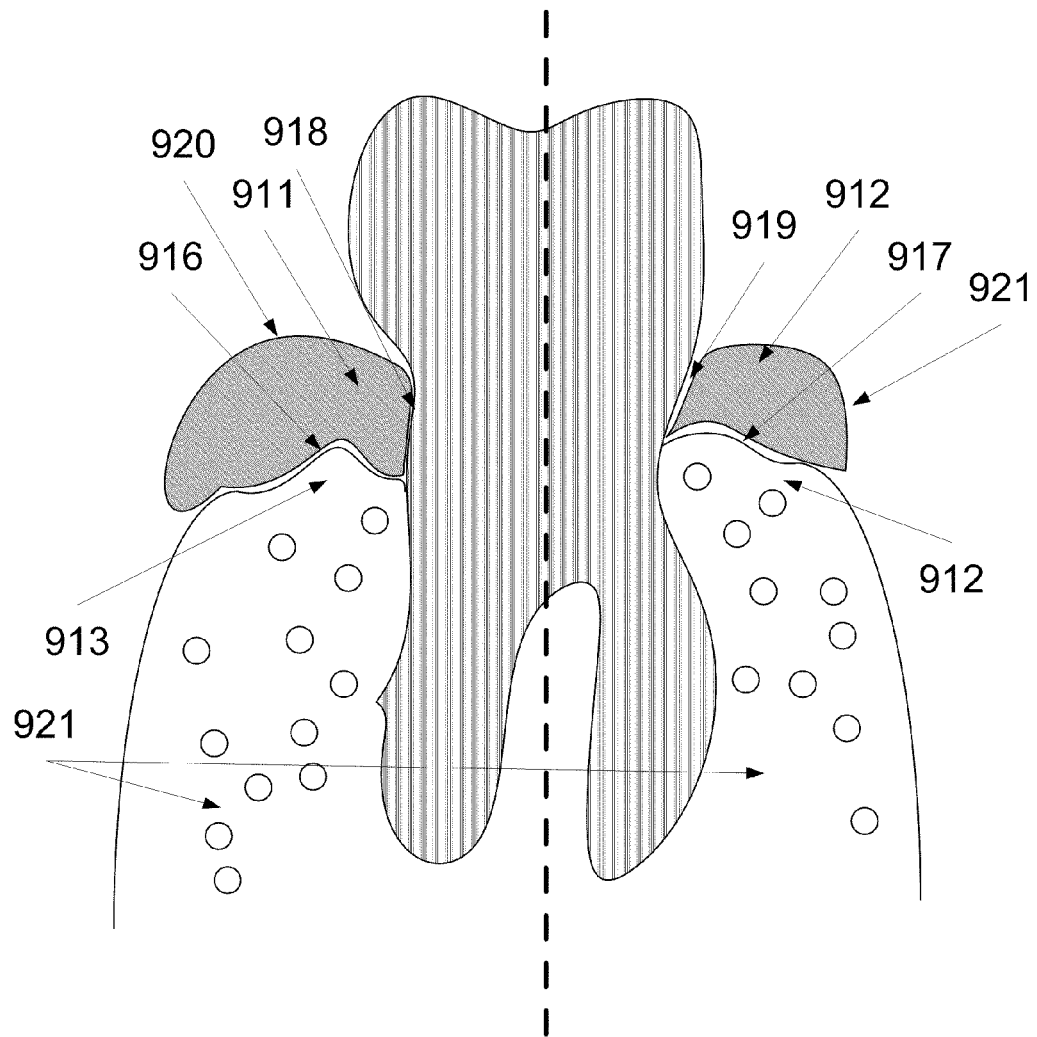
FIG. 9F is a sectional schematic view a pair of exemplary complementary bone grafts, which are implanted to tightly fit a surface of a periodontal bone defect having lingual/palatal and buccal surface portions, according to some embodiments of the present invention.

For clarity, reference is made to FIG. 9F, which is a sectional schematic view a pair of exemplary complementary bone grafts 911, 912, for example as shown at FIGS. 9A-9E, which are implanted to tightly fit a surface of a periodontal bone defect having lingual/palatal and buccal surface portions 913, 914, according to some embodiments of the present invention. The term fit tightly relates to the interface between each bone graft 911, 912 and the periodontal alveolar bone and/or crest 921, for example as respectively shown by numerals 916, 917. The term complementary is referred to the ability of two bone grafts to jointly cover buccal, lingual/palatal, and/or interdental surfaces of one or more periodontal bone defects. The term complementary also referred to the ability of the two bone grafts to encircle a large portion of one or more teeth in the treated area, for example as shown at 918, 919. The term reconstruction refers to the ability to reconstruct, restore and/or otherwise repair the structure of the mandible and/or the maxilla, for example as shown at 920 and 921. It should be noted that the reconstruction may or may not be identical to a surface of a target structure. As the reconstruction of the external surface of the mandible and/or the maxilla, for example as shown at 920 and 921, it does not affect the bone augmentation and therefore the accuracy of the reconstruction may be less crucial.

First, as shown at 100, an imaging data depicting the mandible and/or the maxilla of the patient, or any portion thereof, is acquired. For brevity, the mandible, the maxilla, and/or any portion thereof may be referred to herein, separately or jointly, as the jaws of the patient. Such imaging data optionally includes a three dimensional (3D) representation of the jaws. The imaging data is captured by a 3D modality, such as a micro laser optical device, a computerized tomography (CT) modality, an intra-oral camera, or an ultrasound modality, a magnetic resonance imager (MRI) modality, an MRI-CT (MRT) modality, a cone beam CT (CBCT) modality, a confocal scanning modality, and/or any device that is capable of capturing an intra-oral image of the mouth of the patient. Optionally, the imaging data is acquired from a medical imaging database, such as a picture archiving and communication system (PACS). In such an embodiment the imaging data may be represented as an image of a medical record, such as a digital imaging and communications in medicine (DICOM) object.

As shown at 101, the imaging data is fed to a planning unit for planning one or more dental bone implants having bone graft fitted to reconstruct at least a portion of a treated area of the jaws. As used herein, a treated area means a surface area of the mandible, the maxilla, and/or any portion thereof. The surface area has one or more periodontal bone defects such as dehiscences or fenestrations of the alveolar crest and/or bone, horizontal bone defects, vertical bone defects, burr like holes and/or holes and fractures caused by a periodontal disease.

Optionally, the planning unit generates, based on the image data, one or more models, maps, guidance sets, set of values, equations and/or ranges, and/or files for the manufacturing of the dental bone implants, for brevity referred to herein as dental bone implant models. Each dental bone implant model is based on the surface of the treated area and defines the structure of one or more bone graft that allows reconstructing periodontal bone defects in the treated area. Optionally, the dental bone implant models are generated upon request of a system operator, such as a dentist, a caretaker, or a lab technician. For example, the planning unit may generate a model, optionally three dimensional (3D) that maps the jaws and/or a set of equations and/or values which define the structure of the jaws. A dental bone implant model may be stored as one or more files in a local repository and/or forwarded to a manufacturing unit, for example as described below.

Optionally, the planning unit is executed on a client terminal, such as a personal computer, a laptop, a Smartphone and/or any other computing unit. For example, the planning unit may be installed on a client terminal at a dental clinic. Optionally, the planning unit includes a graphical user interface (GUI) that allows displaying the dental bone implant model and/or the related imaging data, for example on a display, such as a liquid crystal display (LCD) screen of the client terminal. The GUI optionally allows the operator to adjust the dental bone implant models, for example by changing or otherwise adjusting the boundaries thereof according to the imaging data. In such a manner, the user may adjust the dental bone implant models before they are forwarded for manufacturing. Optionally, the operator may apply predefined operators, such as smoothing, rounding and/or lapping operators, for refining the dental bone implant model.

Now, as shown at 102, the dental bone implant models are forwarded to a manufacturing unit, for example as a set of files. As shown at 103, the manufacturing unit generates one or more dental bone implants according to the one or more dental bone implant models.

Optionally, the manufacturing is automatic. Optionally, the manufacturing includes one or more manually controlled sub processes. Optionally, the manufacturing unit comprises a production module for computing a structure defining the size and the shape of the one or more dental bone implants.

Optionally, the manufacturing unit comprises a computer guided production module for allowing a technician to adjust the production process, for example by defining cutting edges and/or construction materials.

As outlined above, each dental bone implant includes one or more fitted bone grafts which are generated according to the each dental bone implant model. Optionally, each dental bone implant includes a pair of complementary fitted bone grafts which are structured to reconstruct treated area around one or more teeth without extracting them. For example, one or more pairs of complementary fitted bone grafts are structured to reconstruct treated area around the maxillary left teeth, namely some or all of the central incisor, lateral incisor, canine, first premolar, second premolar, first molar, second molar, and third molar in the maxillary left portion of the jaws. Additionally or alternatively, one or more pairs of complementary fitted bone grafts may be implanted to reconstruct treated area around the maxillary right teeth, namely some or all of the central incisor, lateral incisor, right canine, first premolar, second premolar, first molar, second molar, and third molar in the maxillary right portion of the jaws. Additionally or alternatively, one or more pairs of complementary fitted bone grafts may be implanted to reconstruct treated area around the mandibular left teeth, namely some or all of the central incisor, lateral incisor, right canine, first premolar, second premolar, first molar, second molar, and third molar in the mandibular left portion of the jaws. Additionally or alternatively, one or more pairs of complementary fitted bone grafts may be implanted to reconstruct treated area around the mandibular right teeth, namely some or all of the central incisor, lateral incisor, right canine, first premolar, second premolar, first molar, second molar, and third molar in the mandibular right portion of the jaws. According to some embodiments of the present invention, a fitted bone graft is structured to reconstruct an edentulous area of the mandible and/or the maxilla of the patient.

Optionally, as outlined above, the complementary bone graft jointly cover one or more periodontal bone defects of the mandible or the maxilla. While one of the bone graft is shaped to fit tightly to a certain portion of the one or more periodontal bone defects the other is shaped to fit tightly to a complementary portion of the one or more periodontal bone defects. Jointly, the bone grafts reconstruct the mandible or the maxilla.

Optionally, some or all of the fitted bone grafts are made of an osteogenetic material. Optionally, some or all of the fitted bone grafts are autografts which involve utilizing bone obtained from the patient receiving the fitted bone graft, such as from the iliac crest, the mandibular symphysis, and/or the anterior mandibular ramus. Optionally, some or all of the fitted bone grafts are allografts which are derived from a human source, such as a fresh bone, a fresh-frozen bone, a freeze-dried bone allograft (FDBA), and/or a demineralized freeze-dried bone allograft (DFDBA). Optionally, some or all of the fitted bone grafts are made of a syntactic material, for example ceramics such as calcium phosphates, for example hydroxyapatite and tricalcium phosphate, bioglass, and calcium sulphate, and/or any biologically active materials, see Hench 'Bioceramics: From Concept to Clinic' 1991, Journal of the American Ceramic Society, which is incorporated herein by reference. Optionally, some or all of the fitted bone grafts are xenografts, which are bone substitutes from a species other than human, such as porcine and bovine sources. Optionally, the fitted bone graft may be an alloplastic which is made from hydroxylapatite, calcium carbonate, tricalcium phosphate, bioactive glass and/or any combination thereof.

Optionally, some or all of the fitted bone grafts are doped, coated, and/or otherwise contain one or more growth factors, for example EMDOGAIN™ Bone Morphogenic Protein (BMP), transforming growth factor (TGF)-P1, insulin growth factor (IGF), fibroblast growth factor FGF, platelet-derived growth factor (PDGF) and epidermal growth factor EGF, ions such as strontium and/or mixed with bone marrow aspirate to increase biological activity, human growth factors, and/or Morphogens, such as bone morphogenic proteins in conjunction with a carrier medium, such as collagen. The regenerative agents allows the bone graft not only to serve as a scaffold for currently existing osteoblasts but will also trigger the formation of new osteoblasts promoting faster integration of the graft bone.

Optionally, some or all of the fitted bone grafts are doped, coated, and/or otherwise contain one or more periodontal regeneration limiting agents which are designed to delay or prevent osteogenetic processes in the bone graft, for example in other to bound the bone augmentation processes to and/or from one or more segments of the bone graft.

Optionally, as further described below, surgical guide is marked and/or drilled on the surface of the bone grafts.

As shown at 104, the dental bone implants are now provided for reconstructing the jaws of the patient, as shown at 105. As further described below, the fitted bone grafts are implanted between the periodontal alveolar bone and/or crest and the gingival tissue of the patient. For brevity, the periodontal alveolar bone and/or crest may be referred to herein as periodontal alveolar bone. The implementation may include anchoring the one or more fitted bone grafts to the periodontal alveolar bone and/or crest and/or to one another using screws or fasteners, for example as further described below. Optionally, the one or more fitted bone grafts are attached to the jaws and/or to one another using cements and/or adhesives, for example glass ionomer, resin cement, zinc phosphate, zinc polycarboxylate, compomer, and/or resin-modified glass.

Figure 2:
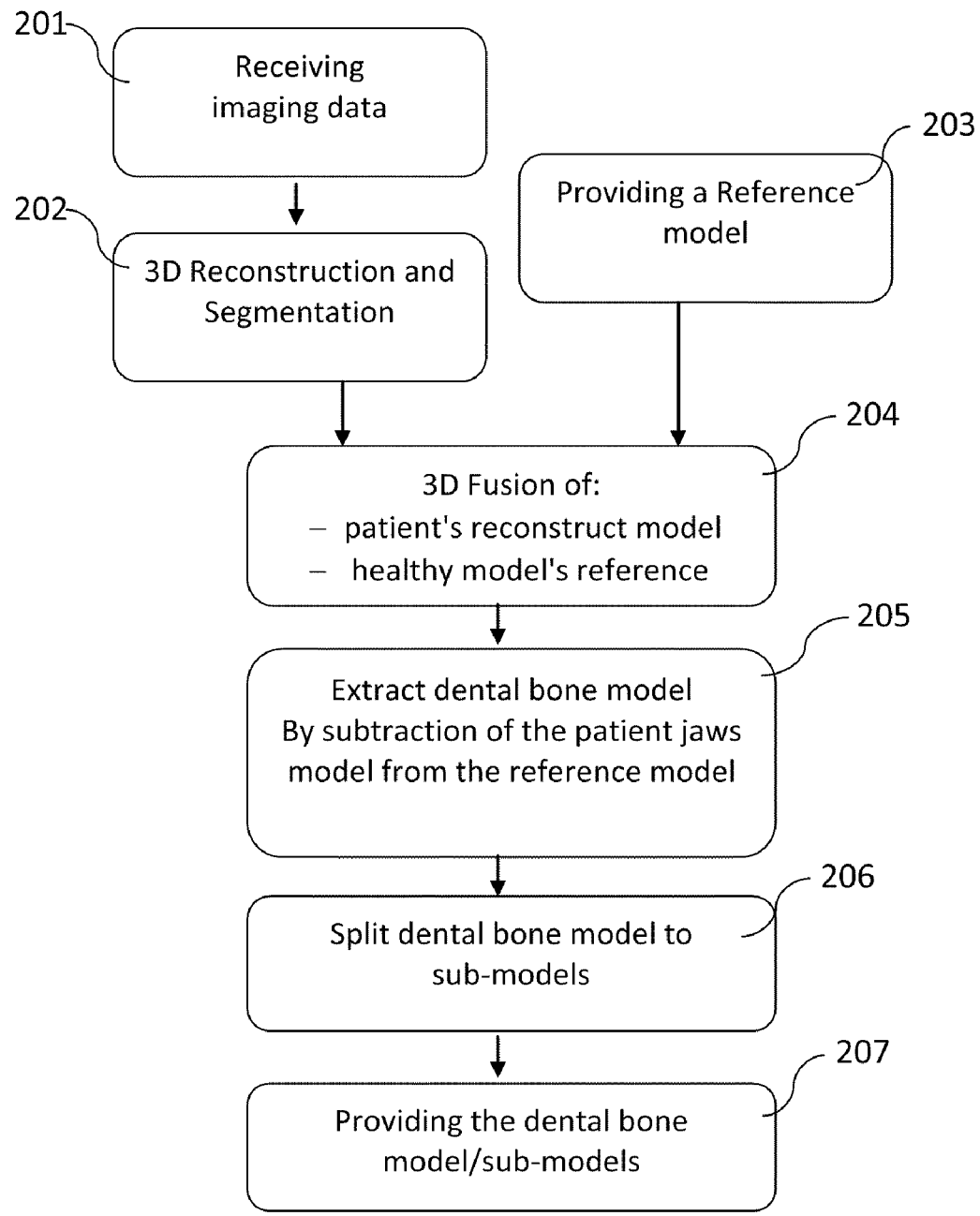
FIG. 2 is a flowchart of a method for planning a dental bone implant having one or more fitted bone grafts for reconstructing one or more periodontal defects in the mandible and/or the maxilla of a patient according to respective imaging data, according to some embodiments of the present invention.

Reference is now made to FIG. 2, which is a flowchart of a method for planning a dental bone implant, having one or more fitted bone grafts, for reconstructing one or more periodontal defects in the mandible and/or the maxilla of a patient according to respective imaging data, according to some embodiments of the present invention.

First, as shown at 201, imaging data depicting the mandible and/or the maxilla of the patient is received, for example as described above.

Then, as shown at 202, a model of the mandible and/or the maxilla of the patient are is created, for example by known reconstruction and segmentation methods. The model is optionally a 3D representation of the anatomical structure of the jaws of the patient, which may be referred to herein as a patient jaws model. The patient jaws model optionally depicts the contours of the surface of the mandible, the maxilla, and/or any portion or combination thereof. Optionally, the patient jaws model further depicts surrounding soft tissues, such as the gingival tissues and/or the existing teeth of the patient. In such an embodiment, the teeth and the soft tissues may be segmented from the mandible, the maxilla, and/or any portion or combination thereof.

Figure 3:
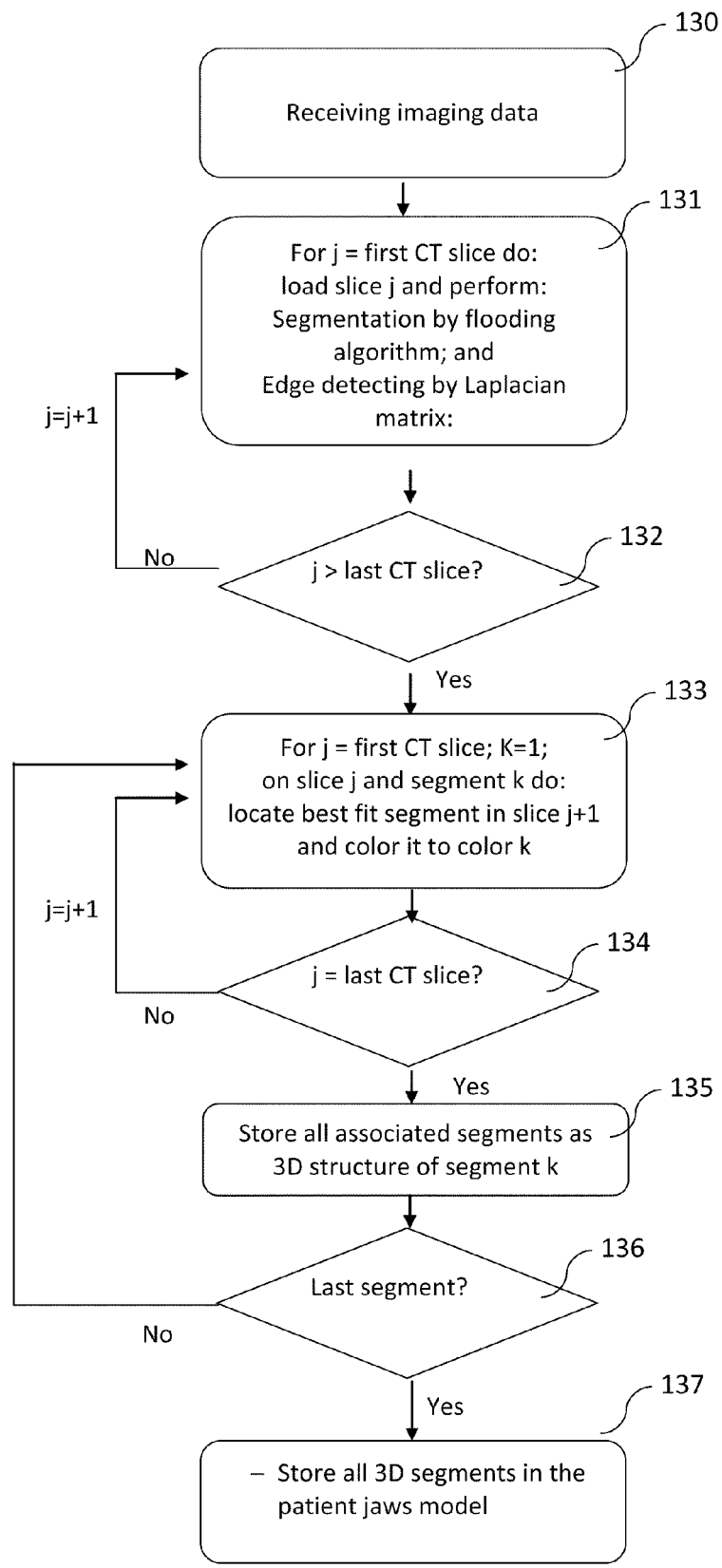
FIG. 3 is a flowchart of an exemplary jaws segmentation process, according to some embodiments of the present invention.

Reference is now made to FIG. 3, which is a flowchart of an exemplary jaws segmentation process, according to some embodiments of the present invention.

First, as shown at 130, the imaging data, which is optionally a CT object, is received. Then, as shown at 131, each slice, denoted herein as j, is separately segmented, for example using a flooding algorithm. In use, the flooding algorithm, which may be referred to herein as a watershed algorithm, divides the slice into a number areas based on the topology of the image it represents. Optionally, the watershed algorithm incorporates an edge detecting process which is optionally performed by a Laplacian matrix. Additionally or alternatively, the segmentation of the slice is performed according to one or more known methods, for example as described in U.S. Pat. No. 7,542,604, which is incorporated herein by reference. As shown at 132, all the slices may be segmented.

After all the slices have been segmented, as shown at 133, some or all of the segments of each CT slice are examined. During the examination, one or more segments in a certain CT slice are separately compared with some or all of the segments of the subsequent CT slice. The best matching segment in the subsequent slice is then associated with the matched segment from the certain CT slice, for example by tagging and/or coloring. For brevity, the tag and/or color denoted herein as $k_1$.

In such an embodiment, the tag and/or color are indicative of the intensity of the signal of the segment. Optionally, a match is found according to the shape of the examined segment. Such a fit may optionally be used to select segments which may be connected and/or having a similar overall shape. As shown at 134, this process is repeated for each one of the slices Now, as shown at 135, all $k_1$ colored and/or tagged segments are stored are combined to create a 3D structure.

As shown at 136, the process depicted in 133-135 is repeated for each set of tagged and/or colored segments which may be sequentially referred to as $K_n$.

After all the 3D structures have been identified, a 3D reconstructed model is outputted as a patient jaw model.

Alternatively, the process of reconstructing the imaging data to form a 3D model of the jaws is performed according to a volume reconstruction method, for example as described in S. Suebnukarn et al., "Interactive Segmentation and Three-Dimension Reconstruction for Cone-Beam Computed-Tomography Images", NECTEC Technical Journal. 2008; 8(20): 154-161, which is incorporated herein by reference. Other methods may be used, for example as described in Barandiaran et. al., an automatic segmentation and reconstruction of mandibular structures from CT-data, VICOMTech, Spain, German Cancer Research Center, Division of Medical and Biological Informatics, and Suebnukarn, et. al. Interactive Segmentation and Three-Dimension Reconstruction for Cone-Beam Computed-Tomography Images, School of Engineering and Technology, Asian Institute of Technology, Klongluang, Pathumthani, Thailand, 12120, which are incorporated herein by reference Reference is now made, once again, to FIG. 2. Now, after, during, and/or before a patient jaws model is created by reconstructing and/or segmenting the data imaging, a reference model of reference jaws, such as healthy jaws or structured jaws for certain pathologies and/or facial bone reconstruction, is received, optionally as a 3D model, for example as shown at 203. Optionally, the reference model is uploaded from a memory of that is accessible to the planning unit. Optionally, the reference model is selected from a database that hosts a plurality of reference models, each depicting reference jaws which are associated with a certain demographic profile, for example age group, race, gender, height, estimated and/or measured jaws dimensions, and the like. In use, the reference model is either selected manually, for example using a GUI and/or automatically by matching between the demographic profiles and medical information pertaining to the patient. Optionally, the reference model is based on imaging data depicting the jaws of the patient in the past. For example, healthy jaws of a patient are imaged so as to create a reference model for future use. In such a manner, the patient assures that her jaws can be reconstructed, for example as outlined above and described below, to their current structure.

Optionally, the reference model is registered, aligned, scaled, and/or otherwise transferred according to the patient jaws model. For brevity, scaling, registering, aligning, transforming, and/or any combination thereof may be referred to as adjusting or registering.

Figure 4:
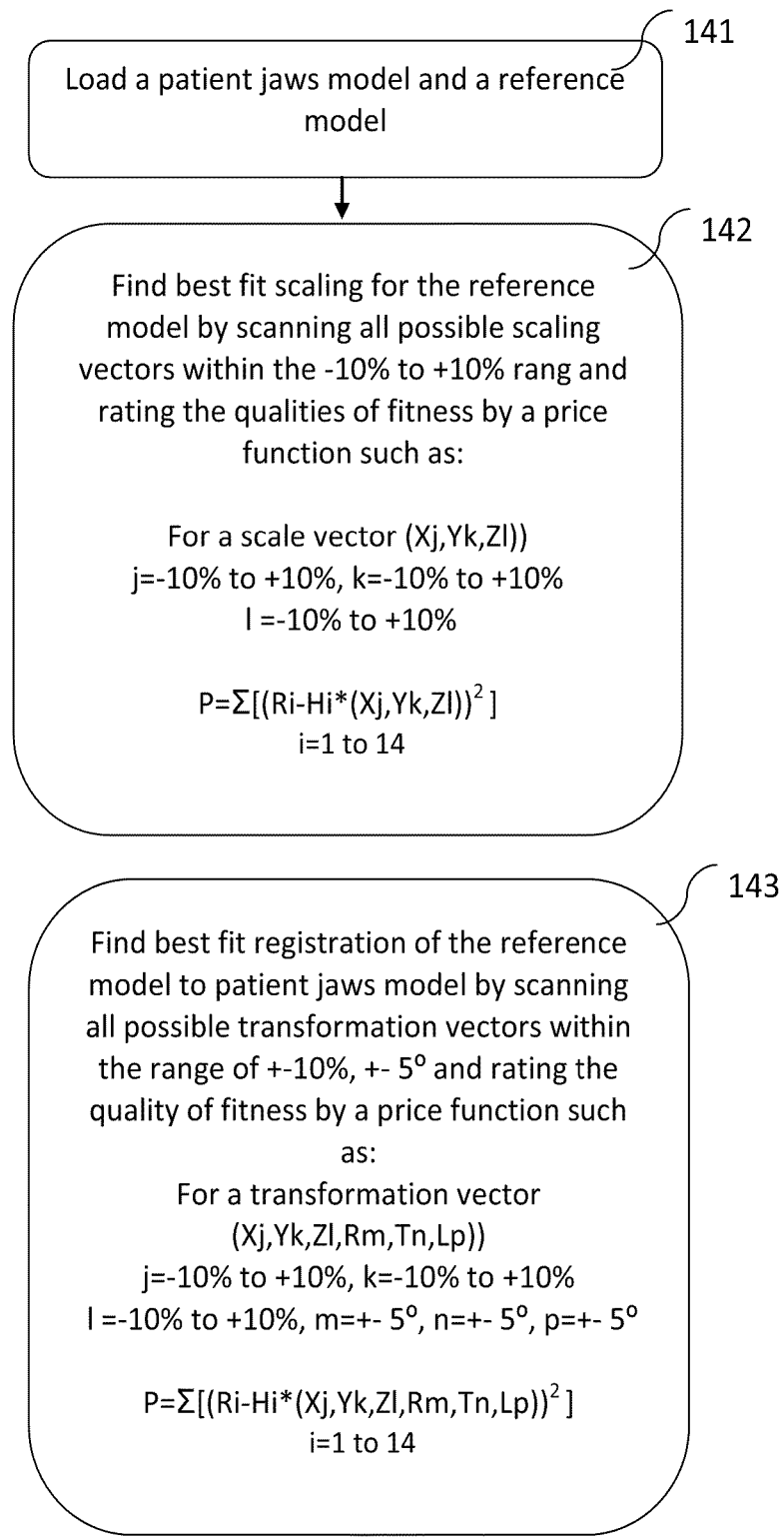
FIG. 4 is a flowchart of a process for adjusting a reference model according to a patient jaw model, according to some embodiments of the present invention.

Reference is now also made to FIG. 4, which is a flowchart of a process for adjusting the reference model according to the patient jaw model, according to some embodiments of the present invention. First, as shown at 141, the patient jaw model and the reference model are received, for example loaded from a medical imaging modality and a repository. Now, as shown at 142, a best fit scaling vector is selected according to a deviation between the models and optionally according to a set of limitations.

Optionally, a plurality of scaling vectors are examined within a particular range, for example between −10% and +10%. The range may be defined differently for different models in the database. One or more fitness parameters are determined for each scaling vector, for example according to a price function, for example:

$$P=\Sigma[(R_i-H_i^*(X_j,Y_k,Z_l))^2]$$  Equation 1 where i denotes a value between 1 and 14, $(X_j, Y_k, Z_l)$ denotes a particular scale vector, j, k and l denotes a range such as a range between −10% and +10%, $R_i$ denotes a tooth number i in the patient jaw model, and $H_i$ denotes a tooth number i in the reference model. The price function centers around a relative location of each tooth in each one of the model according to best fit, for both scaling and shifting. Optionally, the price function may use any best fit function. Once the best scaling vector has been selected, it is applied to the reference model without changing the orientation of the patent jaws model.

Now, as shown at 143, a best fit registration is performed according to the selected best transformation vector, optionally in the light of the requirements of the patient jaws model. This process allows registering the reference model to the coordinates of the patient jaws model by rigid and/or non rigid transformation featuring rotation and translation.

Optionally, the transformation is performed according to a transformation vector which is selected from a plurality of transformation vectors within a particular range, for example between −10% and +10%, optionally further between −5 degrees and +5 degrees. Optionally, one or more parameters of fitness of the transformation vector are determined according to a price function, for example as follows:

$$P=\Sigma[(Ri-Hi^*(X_j,Y_k,Z_l,R_m,T_n,L_p))^2]$$  Equation 2 where i denotes a value between 1 and 14, $(X_j, Y_k, Z_l, R_m, T_n, L_p)$ denotes a scale vector in which (X, Y, Z) denotes translation coefficients and (R, T, L) denotes rotation coefficients, j, k and l denotes variable range values, such as between −10% and +10%, m, n and p denotes variable range values between −5° degrees and +5° degrees. Similarly to the described above, the price function optionally relates to the best fit of the teeth as previously described. Once the best transformation vector has been selected, it is preferably applied to the reference model.

Optionally, the reference module is scaled according to an estimated size of the patient's jaws, for example, according a Euclidean and/or geodesic distance between different reference points on the patient jaws model. Optionally, the reference module is scaled and/or aligned according to data and/or instructions provided by the system operator, optionally via a designated GUI. In such an embodiment, the models may be presented to the operator allowing her to redefine and/or to match the contours of the reference model to the contour of the patient jaws model.

Reference is now made, once again, to FIG. 2. Now, as shown at 205, a dental bone implant model is formed based on the space between the scaled and aligned reference model and the patient jaw model. Optionally, the dental bone implant model is formed by a 3D fusion of the reference model and the patient jaw model. The dental bone implant model is created to adjust the scale, size and other factors of the reference model to be suitable for comparison to the patient's model. Optionally, the dental bone implant model is created by subtracting and/or eliminating segments from a copy of the reference model according to the surface of the patient jaw model. Some or all of the subtracted segments correspond with the surface of the hard tissues which are documented in the patient jaw model, for example the surface of the periodontal alveolar bone and/or crest of the mandible and/or the maxilla of the patient. Optionally, the tooth sockets in the reference model are filled as if they contain periodontal alveolar bone and/or crest tissue. In such a manner, a deviation between the tooth sockets in the patient jaws model and the reference model does not create unnecessary niches or recesses in the produced dental bone implant.

Optionally, some of the subtracted segments correspond with soft tissues which are documented in the patient jaw model.

The dental bone implant model, which includes the remaining segments of the subtracted reference model, represents a structure that fills the one or more periodontal bone defects of the periodontal alveolar bone and/or crest portion of the mandible and/or the maxilla of the patient. This filling completes the parts which are missing between the reference model, which optionally define the surface of a healthy mandible and/or the maxilla and the patient jaw model that define the actual surface of the mandible and/or the maxilla of the patient.

Figure 5:
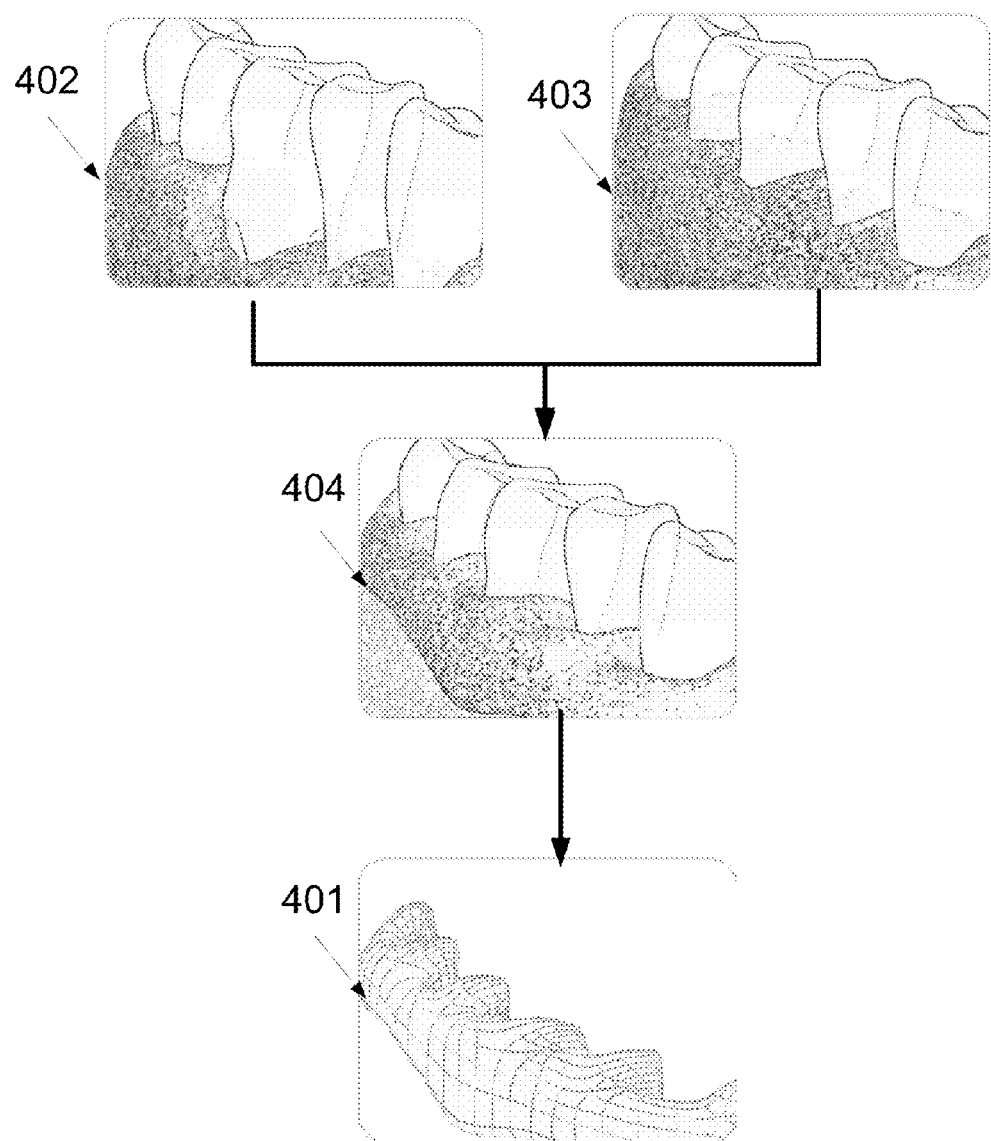
FIG. 5 is pictorial illustration of the data that is used for creating a dental bone implant model, according to some embodiments of the present invention.

Reference is now also made to FIG. 5, which is pictorial illustration of the data which is used for creating the dental bone implant model 301 and of the dental bone implant model 301, according to some embodiments of the present invention.

Numeral 402 depicts a patient jaw model that is based on imaging data of a portion of the mandible of the patient. The imaging data may be obtained from a craniofacial imaging modality, such as CBCT modality. The imaging data may be provided as a set of consecutive slices of the jaws and/or as a volumetric representation of the structure of the patient' jaws. The imaging data may be obtained via a DICOM interface, which the standard thereof is incorporated herein by reference.

The patient jaw model is created using known 3D reconstruction and segmentation processes, for example as described above. The patient jaw model depicts the periodontal bone defects of the jaws depicted in the imaging data.

Numeral 403 depicts an exemplary reference model, which is optionally selected according to the medical information of the patient. The reference model 402 is optionally scaled, registered and/or aligned according to the size and/or orientation of the bones depicted in the patient jaw model. For example, numeral 402 depicts a 3D model of a typical healthy bone condition, which is scaled and aligned, according to the patient jaws model.

Numeral 404 depicts an exemplary 3D fusion between the models 402, 403. This fusion allows generating the dental bone implant model 401, for example as described above. Optionally, the dental bone implant model 401 is rounded, for example as shown at 402. In such a manner, sharp edges of the dental bone implant model are removed. The dental bone implant model 401 may be adjusted according to various criteria and/or parameters of the biocompatible material from which the dental bone implant may be produced.

Figure 6:
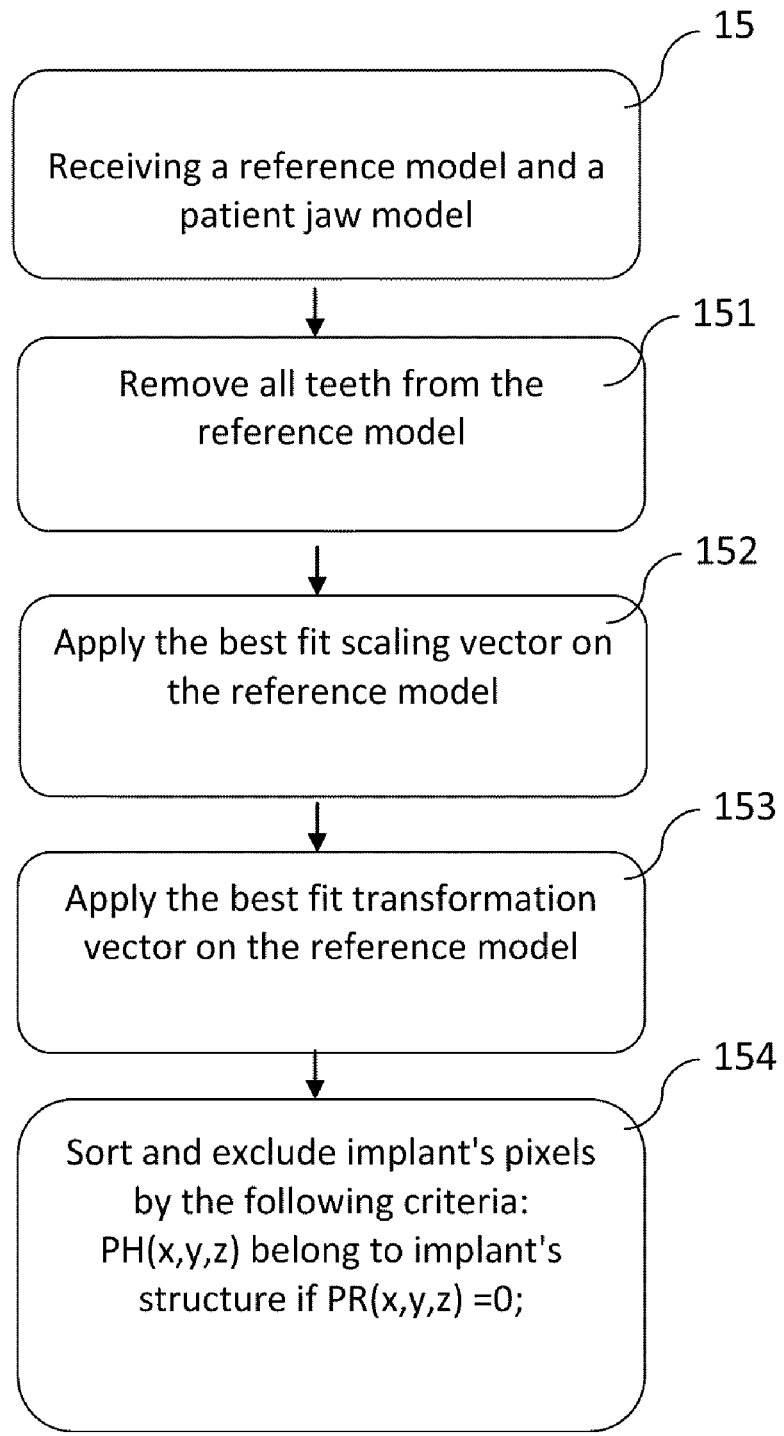
FIG. 6 is a flowchart of a process for creating the dental bone implant model after fusing the reference model onto the patient jaw model, according to some embodiments of the present invention.

Reference is now also made to FIG. 6, which is a flowchart of a process for creating the dental bone implant model after fusing the reference model onto the patient jaw model, according to some embodiments of the present invention.

First, as shown at 150, a full reference model, optionally adjusted as described above, is received. The full reference model depicts reference teeth and soft tissues, in addition to the hard tissue. Now, as shown at 151, all teeth are removed from the full reference model. Now, as shown at 152, a best fit scaling vector, for example obtained as described in relation to FIG. 4, is applied to the reference model. As shown at 153, the best fit transformation vector, for example obtained as described in relation to FIG. 4, is applied to the reference model. Now, as shown at 154, the models are compared, fused and subtracted by eliminating the positions at which the patient jaws model indicates a spatial presence of a periodontal alveolar bone and/or crest from the reference model. For example, the pixels of the dental bone implant model are defined as follows: $P_H(x,y,z)$ is marked as part of the dental bone implant if $P_R(x,y,z)=0$ where $P_H$ denotes pixels related to the reference model and $P_R$ denotes pixels related to the patient's model. Thus, only pixels which are present in the reference model and absence from the patient jaws model are assigned to the dental bone implant model.

Figure 7A:
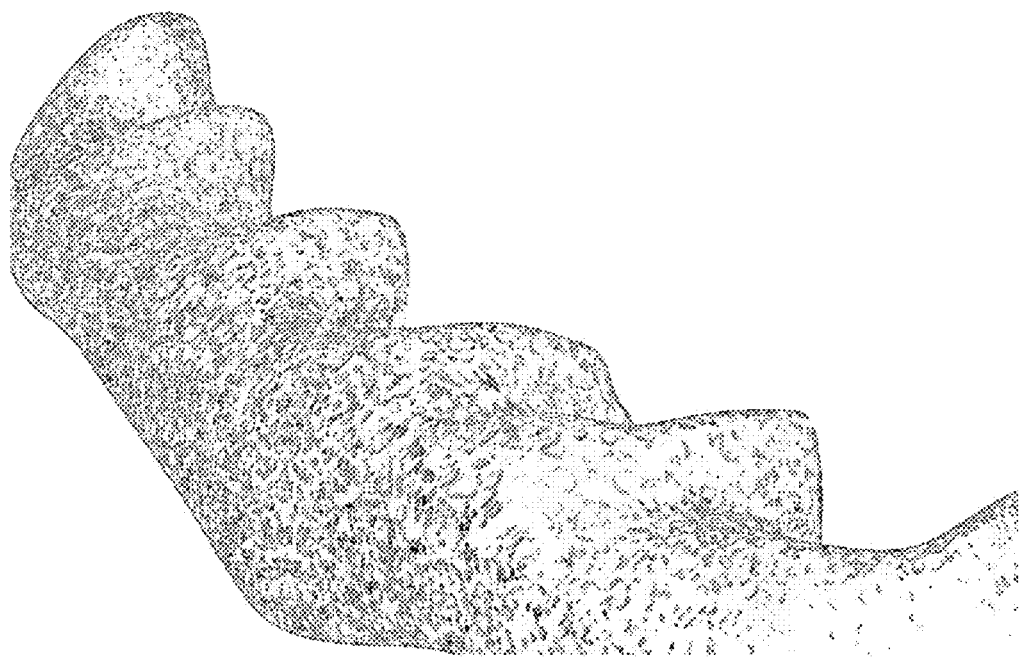
FIGS. 7A and 7B respectively depict a exemplary surface of a portion of a mandible that a dental bone implant created according to the dental bone implant model is intended to repair and/or restore and a schematic illustration of cross section of the dental bone implant, created according to some embodiments of the present invention.
Figure 7B:
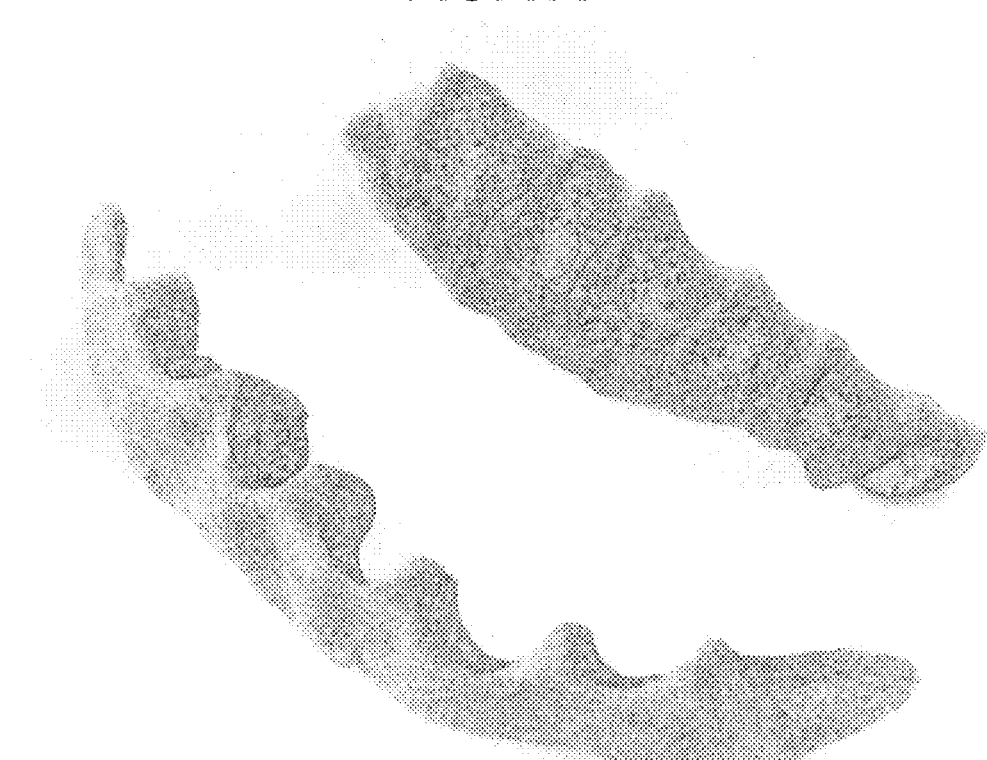

Reference is now also made to FIGS. 7A and 7B, which respectively depict a exemplary surface of an exemplary treated area, namely a portion of a mandible that a dental bone implant created according to the dental bone implant model is intended to repair and/or restore and a schematic illustration of a cross section of the dental bone implant, created according to some embodiments of the present invention. As shown, the mandible surface has multiple periodontal bone defects, some relatively small. The dental bone implant model allows creating one or more fitted bone grafts, for example as out lined above which are fitted to fill the periodontal bone defects. The fitted bone grafts allows repairing, replacing and/or reconstructing one or more tooth sockets of the mandible and/or the maxilla without removing teeth which are supported by it, for example as described below. Additionally or alternatively, the fitted bone grafts allows restructuring and/or reconstructing all the tooth sockets in the treated area. Clearly, dental bone implants may be fitted to other treated areas of the mandible, the maxilla, and/or any portion thereof.

Reference is now made, once again, to FIG. 2. Now, as shown at 206, the dental bone model may be split to form a plurality of dental bone sub-models. Optionally, the splitting is performed according to one or more manufacturing requirements, for example according to manufacturing limitations, such as the biocompatible materials which are used to prepare the dental bone.

Figure 8A:
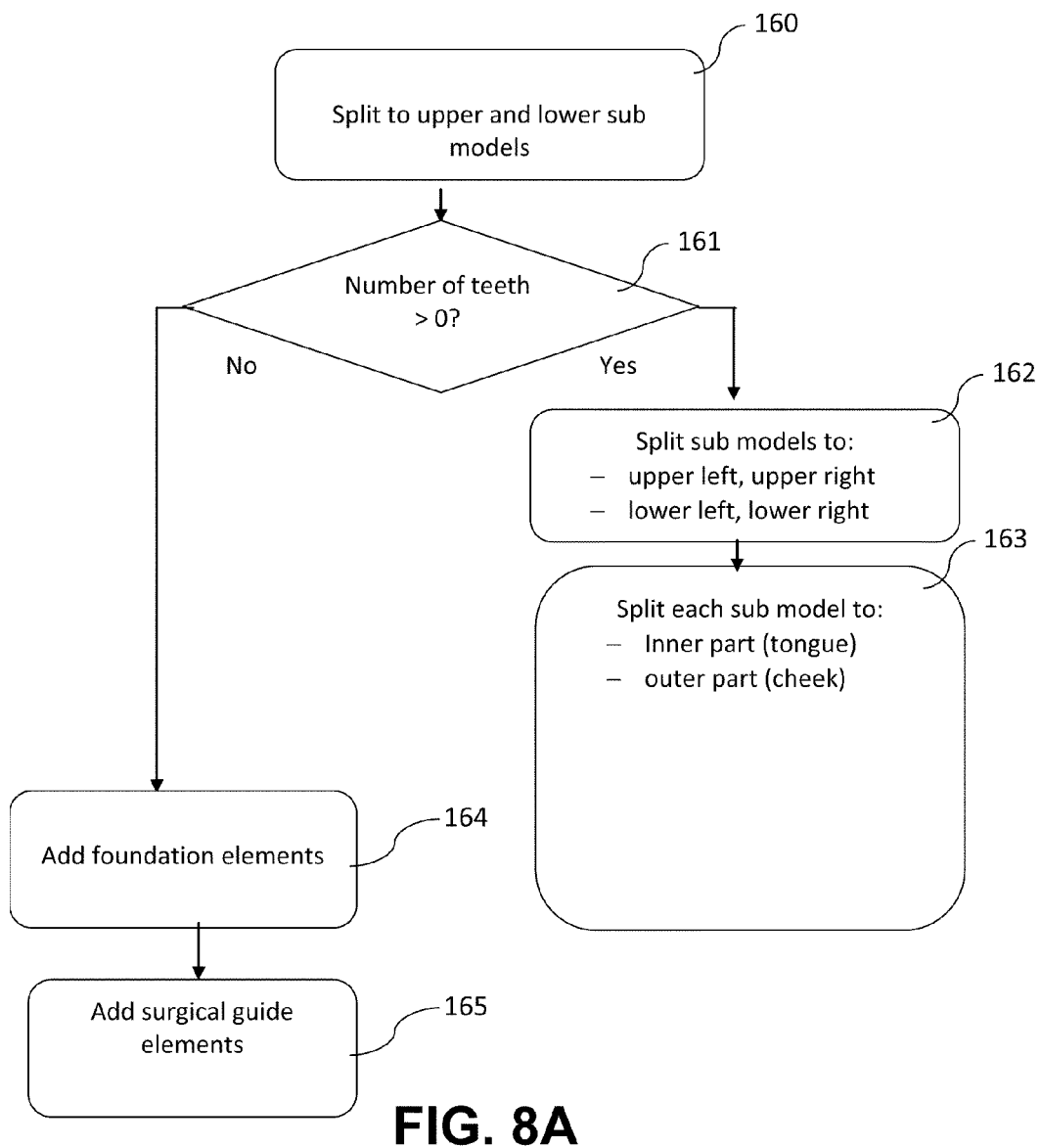
FIG. 8A is a flowchart of a process for determining whether to split a dental bone model to a number of sub models and splitting a dental bone implant model accordingly, according to some embodiments of the present invention.

Reference is now made to FIG. 8A, which is a flowchart of a process for determining whether to split a dental bone model to a number of sub models and splitting a dental bone implant model accordingly, according to some embodiments of the present invention.

Figure 8C:
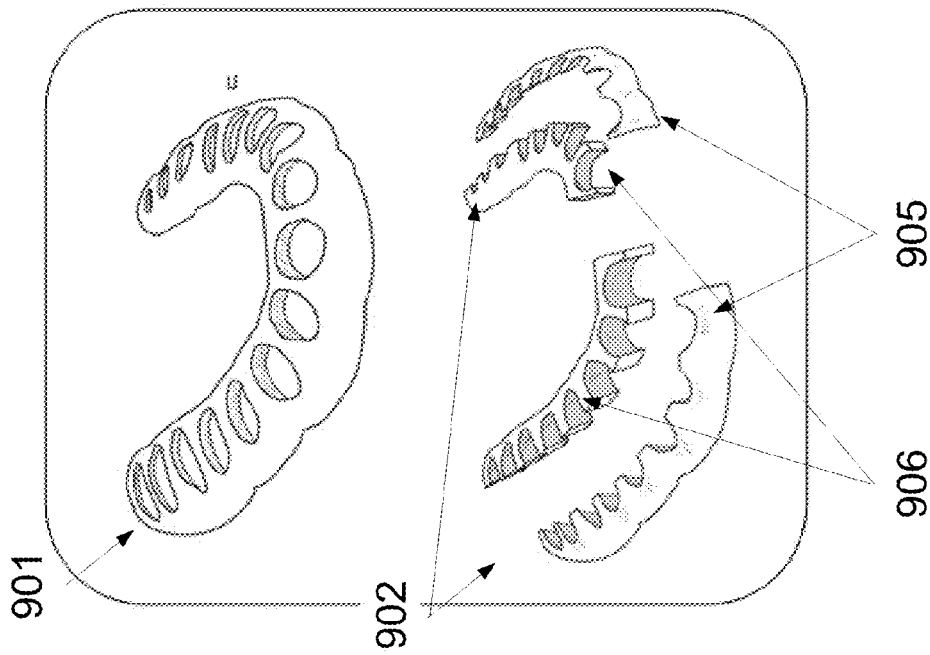
FIGS. 8B and 8C depicts exemplary bone grafts which are generated according to dental bone implant models and/or sub models, according to some embodiments of the present invention.

First, as shown at 160, if the treated area includes both the mandible and the maxilla, the dental bone implant model is split into a mandible sub model and a maxilla sub model which may be referred to as upper and lower sub models. For example, FIG. 8B and numeral 901 of FIG. 8C depict bone grafts generated according to mandible sub models.

Now, as shown at 161, the number of teeth in the treat area is evaluated in each one of the upper and lower sub models. If one or more teeth are present in the treated area, as shown at 162, the dental bone implant model is split into a number of sub models. For each one of the mandible and the maxilla sub models or for a dental bone implant model that define only one of them, the spread of the treated area is checked. If the treated area includes both the right and the left side of the mandible or the maxilla, the sub models and/or the received model is split into left and right sub models. For example, a maxilla sub model is split to a left maxilla sub model formed to complete periodontal bone defects in the left side of the maxilla and a right maxilla sub model formed to complete periodontal bone defects in the right side of the maxilla. For brevity, each one of these sub models may be referred to herein as a lateral jaw sub model.

Now, as shown at 163, each sub lateral jaw sub model is preferably divided into a buccal (outer) part and a lingual/palatal (inner) part, for example to a buccal lateral sub model that is formed to complete periodontal bone defects in the buccal surface of the treated area and a lingual/palatal lateral sub model that is formed to complete periodontal bone defects in the lingual/palatal surface of the treated area. For clarity buccal and lingual/palatal surface may include some or the entire interdental surface that is connected thereto.

Optionally such a splitting is performed by calculating the center of each tooth in the model, defining a cutting line through the centers of the teeth, and splitting along the cutting line, optionally until the lateral sub model is been completely divided to buccal lateral sub models. Such sub models allows creating complementary bone graft that substantially encircle the one or more teeth in the treated area, for example cover at least 60% of one or more of perimeter of each teeth, at least 70% of one or more of perimeter of each teeth, at least 80% of one or more of perimeter of each teeth, at least 90% of one or more of perimeter of each teeth, 100% of one or more of perimeter of each teeth, and/or any intermediate value. The placing of such bone grafts does not require tooth extractions before implantation. For example, FIG. 8C depicts bone grafts generated according to left and right mandible sub models 902 which are spitted to buccal and lingual/palatal lateral sub models 905, 906.

Figure 8B:
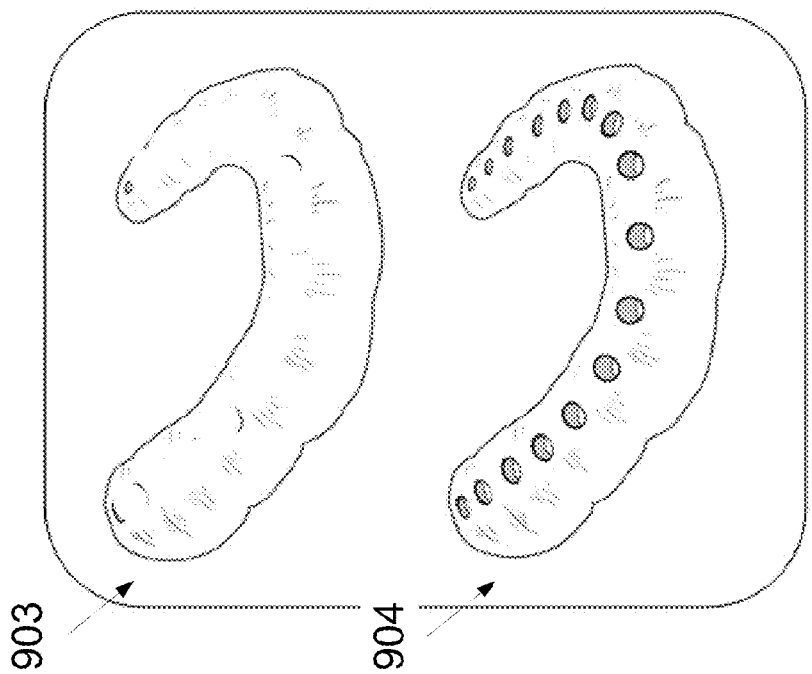

If no teeth are found in the dental bone implant model, the dental bone implant model is only split into a mandible sub model and a maxilla sub model. For example, FIG. 8B depicts a bone graft generated according to a mandible sub model. In such an embodiment, the dental bone implant model defines a single structure that reconstructs periodontal bone defects in the periodontal alveolar bone and/or crest of the maxilla or the mandible.

Now, as shown at 164, one or more recesses for tooth implants may defined in the sub models, for example as shown in numeral 904 of FIG. 8B. In such a manner the model may instruct the generation of a dental bone implant with elements that allow straight forward integration of tooth implants.

As shown at 165, a surgical guide that includes one or more surgical instructions, such as placement of tooth implants which are about to by added to the bone graft, one or more anchoring instructions and placing instructions, are added in respective location to each one of the sub model. In such a manner, the sub model allows creating bone grafts that incorporate surgical guide markings, recesses, extensions and/or bores which are indicative to one or more drilling locations and/or dental implant locations when the bone graft is placed on the treated area. The surgical guide is optionally defined according to the structure and/or the surface of the sub model and/or the respective portion of the treat area. For example, the surgical guide includes anchoring instructions, such as drilling location marking, drilling depth marking, dental screw caliber marking and the like. In use, the surgical guide may be added as one or more visible and/or tactile markings, recesses, bores and/or any other surgical indication.

Reference is no made, once again, to FIG. 2. Now, as shown at 207, the dental bone model and/or the dental bone sub-models are provided to allow the generation of one or more fitted bone grafts. Each sub model may be used as a set of instructions and/or a map for generating a fitted bone graft for reconstructing a segment of a treated area or segments of the treated area. As shown at numeral 102 of FIG. 1, the dental bone model or the dental bone sub-models may be exported to a manufacturing facility, such as a dental implants laboratory, that produces the fitted bone grafts accordingly. The one or more models may be forwarded, optionally after being stored in a file format, over a communication network, such as the internet and/or stored in a portable media.

According to some embodiments of the present invention, as outlined above, the dental bone implant model may be used to create a dental bone implant that is implanted to repair and/or reconstruct one or more tooth sockets without having to remove the teeth they support. In such embodiments, the fitted bone grafts of the dental bone implant may encircle each one of the teeth of the patient when implanted and/or reconstruct segments of tooth sockets which are located in buccal surface of the jaws, the lingual/palatal surface of the jaws and/or in the space between the teeth.

Reference is now made to FIGS. 9A-9C, each is a schematic illustration of an exemplary row of teeth 501-503 and a pair of complementary fitted bone grafts 504-506, each respectively fitted to at least the buccal surface and at least the lingual/palatal surface of periodontal alveolar bone and/or crest that surrounds the row of teeth 501-503, according to some embodiment of the present invention. It should be noted that each one of the bone graft may be individually placed to reconstruct a periodontal bone defect on the alveolar bone of the treated area, optionally around one or more teeth. Each fitted bone graft is optionally made based on a sub model, for example as defined above. Such a pair of fitted bone grafts may be fitted to reconstruct any portion of the mandible or the maxilla without removing teeth, such as a row of teeth 501-503. One of the fitted bone grafts, for example 507, is fitted according to the buccal surface of a periodontal alveolar bone and/or crest around one or more teeth and a pairing fitted bone graft, for example 508, is fitted according to the lingual/palatal surface of the periodontal alveolar bone and/or crest around the same teeth. These fitted bone grafts are designed to reconstruct a significantly eroded periodontal alveolar bone and/or crest of a portion of the mandible that supports a straight row of teeth. The fitted bone grafts 507 508 are fitted to fit together under the gum tissue that surrounds the straight teeth row so as to restore the eroded portion of the mandible.

One or more of the pairing fitted bone grafts is formed to reconstruct a periodontal bone defect between the buccal and lingual/palatal surfaces, for example between the teeth. In such an embodiment, the fitted bone graft has an extension that is formed to be implanted between the teeth, for example as shown at 509. Additionally or alternatively, one or more of the fitted bone grafts is formed to reconstruct a full tooth socket, for example as shown at 510. In such an embodiment, the fitted bone graft may be used as a scaffold for regeneration of bone cells from the periodontal alveolar bone and/or for supporting a dental implant. Optionally, the fitted bone grafts are formed to support a number of tooth implants, which may be sequential or non sequential tooth implants, for example as shown at 511. In such an embodiment, the fitted bone grafts are formed to support the missing tooth implants intermittently. In such a manner, a pressure that is applied on two sequential or proximate teeth crowns is divided between the two supporting fitted bone grafts. As depicted in FIGS. 9A-9C, a pair of fitted bone grafts allows reconstructing various periodontal bone defects so as to recover from different dental pathologies. The pair of fitted bone grafts reinforces the support of the teeth they encircle and reduce or eliminate the space in which caries or any other dental pathology may be developed.

As outlined above, different fitted bone grafts of a common dental bone implant may be generated according to sub models of a common dental bone implant model. In use, during the model generation process, for example in 206, the sub models are created by longitudinally splitting the dental bone implant model. Optionally, the splitting takes into account segments which are designed to reconstruct full tooth sockets, for example as depicted in FIG. 9B and FIG. 9C. In such a manner, an extension for a complete tooth socket is formed in one of the fitted bone grafts rather than two extensions for about half a tooth socket in each one of the fitted bone grafts. Optionally, the complete tooth socket extensions are created intermittently between the complementary fitted bone grafts. In such a manner sequential tooth implants are supported by different bone grafts so that the pressure which they apply on the jaws is split between the bone grafts.

Reference is now made to FIGS. 9D-9E are schematic illustrations of exemplary edentulous jaws surfaces 551, 552 and respective fitted bone grafts 553, 554 which are fitted to restore all the teeth sockets, according to some embodiment of the present invention. The fitted bone graft depicted in 553 allows reconstructing all the teeth of a certain portion of the mandible and the fitted bone graft depicted in 554 allows reconstructing all the teeth of the mandible.

Similarly to the described above, the fitted bone grafts 553, 554 are inserted under the gum tissue so as to restore the eroded bone with sockets which are formed to receive tooth implants.

Figure 10:
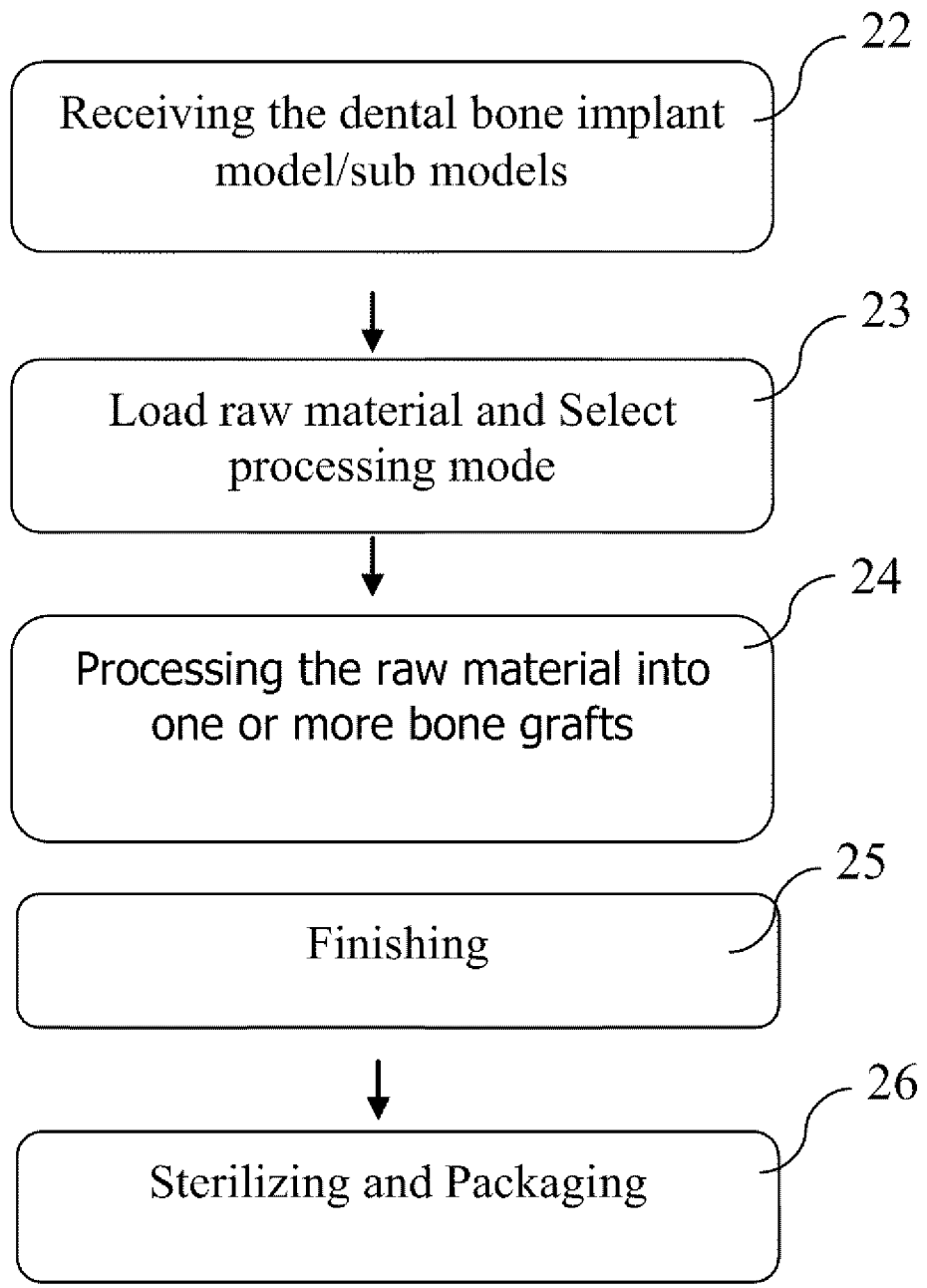
FIG. 10 is a flowchart of a process of generating a bone dental implant according to a model and/or a number of sub models, according to some embodiments of the present invention.

Reference is now made to FIG. 10, which is a flowchart of a process of generating a bone dental implant according to a model and/or a number of sub models, according to some embodiments of the present invention.

First, as shown at 22, the bone dental implant model is received.

Figure 11:
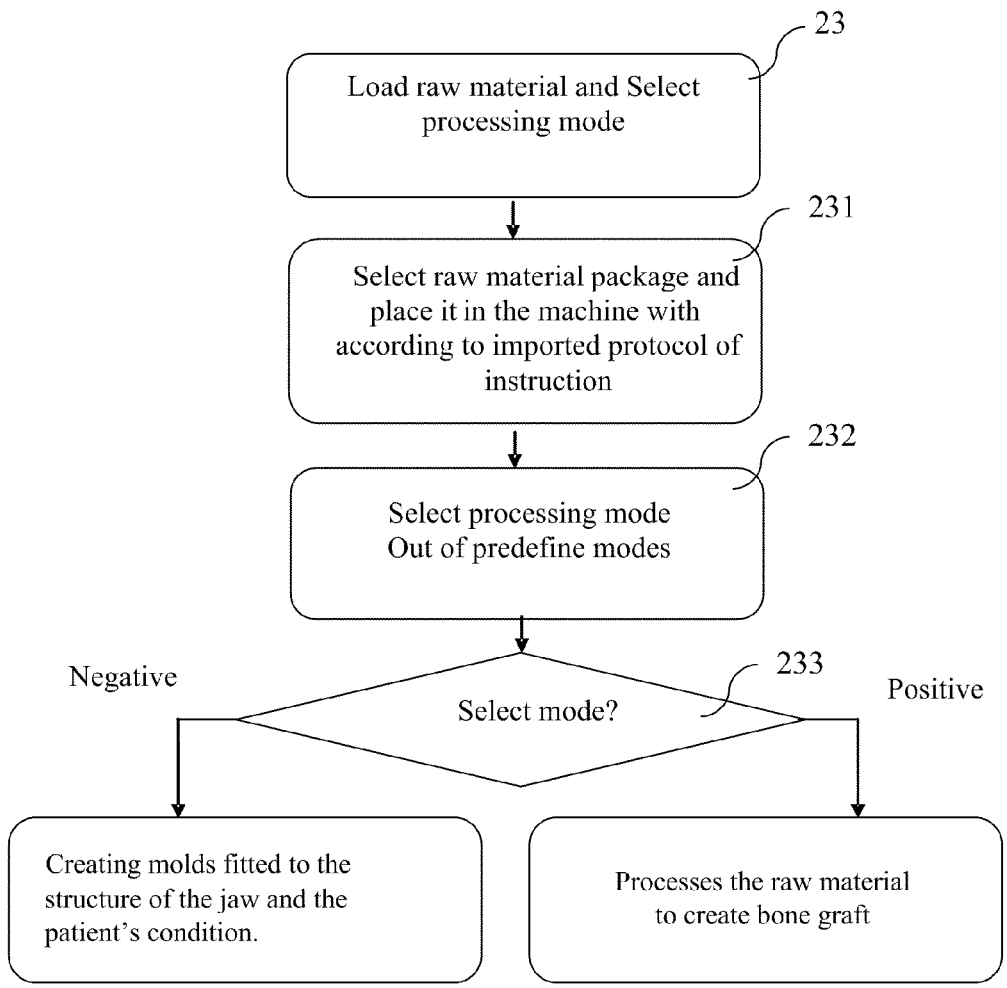
FIG. 11 is a flowchart of a process for selecting and preparing a raw material for a bone graft generation, according to some embodiments of the present invention.

In addition, as shown at 23, the type of the raw material that is used to create the fitted bone grafts is provided and optionally preprocessed. Reference is now made to FIG. 11, which is a flowchart of a process for selecting and preparing a raw material for a bone graft generation, according to some embodiments of the present invention.

First, as shown at 231, a raw material is optionally selected so as to allow the loading thereof into a manufacturing unit according to a respective instruction protocol. Optionally, the raw material comprises a block of material from which the fitted bone grafts are cut, which is also known as mill blank. The mill blank is made of any suitable material that may be carved according to the dental bone model and/or sub modes. Various non-limiting examples of such materials that are known from the art, for example a ceramic material, VITA CELAY™ Vitablocks™, VITA NCERAM™ and Vita Mark II ceramic and/or porcelain blanks from Vita Zahn Fabrik, Bad Sackingen, Germany, MACOR™ micaceous ceramic blanks from Coming, DICOR™ micaceous ceramic blanks from Dentsply, a ceramic silica material as described in U.S. Pat. No. 4,615,678 which is incorporated herein by reference, an improved ceramic dental mill blank which is described in U.S. patent application Ser. No. 09/383,560, filed Aug. 26, 1999 and in U.S. Pat. No. 7,255,562, which are incorporated herein by reference. Other materials may also be used as raw materials, for example materials which are pressed, compressed, poured, and/or gelled to form the fitted bone grafts according to the dental bone implant model and/or sub models.

Optionally, the material selected has the desired degree of hardness and durability, and strength, for example so as to be comparable to a natural mandible or maxilla. Also preferably the material encourages bone growth into its structure, so that the periodontal alveolar bone and/or crest tissue of the patient may become fused in an interlocking manner with the fitted bone graft.

Now, as shown at 232, a processing mode is selected according to the selected material. In such a manner the manufacturing unit can adapt the manufacturing process to the selected raw material. Optionally, the selected manufacturing process mode is a mold mode in which one or more molds, which are fitted according to the dental bone implant model and/or sub models, are used. In use, the raw material is poured into and/or placed in the fitted molds. Optionally, the raw material which is used for molds is an osteogenetic liquid, an osteogenetic gel, and/or a semi-solid osteogenetic raw material. Optionally, the raw material is in a powder form, such as bone powder, titanium grains, a biocompatible powder and/or a combination thereof. This process may be referred to herein as a negative and/or constructive process mode.

Optionally, the selected manufacturing process mode is a shaping mode in which the fitted bone graft is generated by carving, cutting, and/or stamping a mill blank and/or any other osteogenetic raw material according to the dental bone implant model and/or sub models. Such curving may be performed using a light emitter that shapes the mill blank by irradiating laser according to a pattern that is defined according to the dental bone implant model and/or sub models. This process may be referred to herein as a positive and/or destructive process mode.

Optionally, as shown at 233, the processing is performed according to the selected mode.

Optionally, in use, the manufacturing unit receives the dental bone implant model and/or sub models from the planning unit, either locally and/or via a computer network and/or a portable media, such as a CD. The model may be provided as a set of instructions Optionally, the manufacturing unit processes the raw material to produce the fitted bone grafts according to one or more instructions which are locally provided by the system operator, for example via an MMI and/or planned changes to the patient's anatomy, for example due to surgery. Optionally, when in positive process mode, the processing is performed using a dental milling machine, for example such as a CEREC 2™ machine of Siemens (available from Sirona Dental Systems; Bensheim, Germany), a VITA CELAY™ machine (available from Vita Zahn Fabrik; Bad Saickingen, Germany), a PRO-CAM™ machine (Intra-Tech Dental Products, Dallas, Tex.), and PROCERA ALLCERAM™ machine (available from Nobel Biocare USA, Inc.; Westmont, Ill.), which the specifications thereof is incorporated herein by reference. Optionally, a computer added planning module is used for allowing the operator to control the process for example as described in U.S. Pat. Nos. 4,837,732, 4,575,805 and 4,766,704, which are incorporated herein by reference. Such machines may be used for automatically produce the fitted bone grafts by cutting, milling, and grinding a mill blank block according to the dental bone implant model and/or sub models.

Reference is now made, once again, to FIG. 10 Now, after the raw material is selected and processed accordingly, as shown at 24, the fitted bone grafts of the dental bone implant are finalized, for example by smoothing edges and/or polishing, as shown at 25. Optionally, the fitted bone grafts are cleaned of shavings and sharp edges with the use of water, grit and/or sand.

Optionally, the finishing includes adding one or more surgical guidance elements, such as one or more anchoring instructions markings on the fitted bone grafts, for example according to the aforementioned dental bone implant model and/or sub models.

Additionally or alternatively, the one or more fitted bone grafts are coated with a tissue barrier membrane for guiding bone tissue regeneration and to prevent epithelium, for example as described in Duskova M et. al, "Guided tissue regeneration, barrier membranes and reconstruction of the cleft maxillary alveolus". J Craniofac Surg 19 (6): 1153-60 (November 2006), which is incorporated herein by reference.

Now, as shown at 26, the dental bone implant is cleaned, sterilized or otherwise prepared and packaged for shipment and/or storage, optionally automatically. The method of sterilization and/or packaging is adapted to the type of raw material which is used in the process. For example, the bone graft may be sterilized be a sterilizing radiation, such as electron beams, X-rays, gamma rays, or subatomic particles, for example as described in Trends in Radiation Sterilization of Health Care Products, IAEA, Vienna, 24 Sep. 2008, which are incorporated herein by reference.

Figure 12:
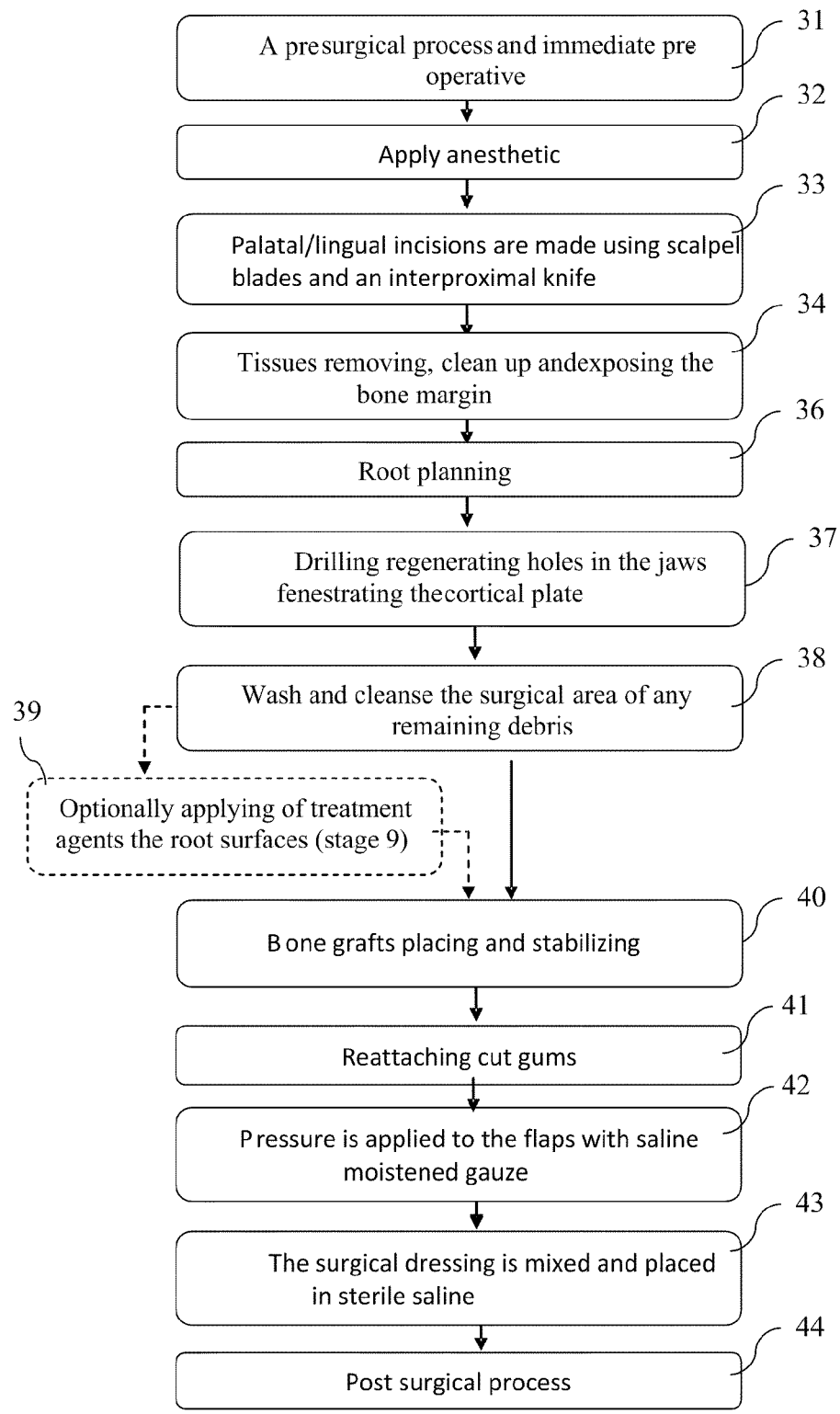
FIG. 12 is a flowchart of an implantation procedure for reconstructing periodontal bone defects by implanting a dental bone implant having one or more fitted bone grafts, according to some embodiments of the present invention.
Figures 13A, 13B:
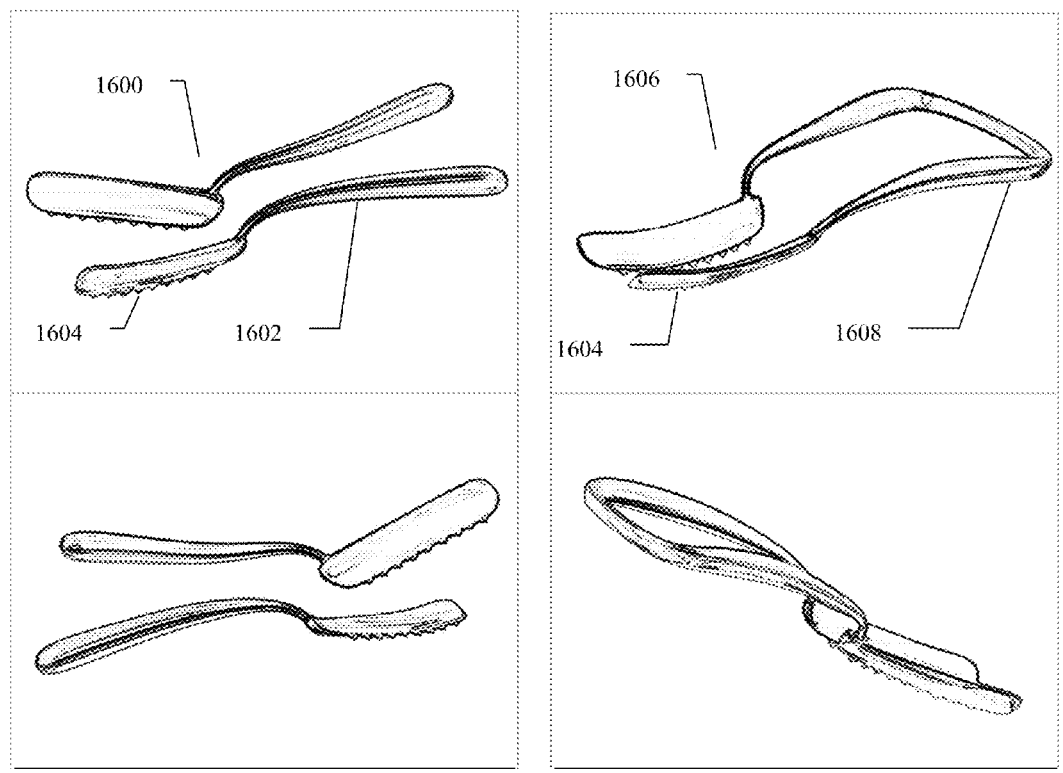
FIGS. 13A-13P are pictorial illustrations of an exemplary implantation procedure, performed according to some embodiments of the present invention.

Reference is now made to FIG. 12, which is a flowchart of an implantation procedure, which may be referred to as a periodontal flap surgery, for reconstructing one or more periodontal bone defects by implanting a dental bone implant having one or more fitted bone grafts, according to some embodiments of the present invention. Reference is also made to FIGS. 13A-13P, which are pictorial illustrations of an exemplary implantation procedure performed according to some embodiments of the present invention.

First, as shown at 31, a pre-surgical process is performed. During this pre-surgical process, the periodontal flap surgery is planned, for example according to the health status and/or pathologies of the patient. Optionally, during this process, a dental bone implant may be prepared as described above. Optionally, during this process, a presurgical phase I therapy involving oral hygiene instruction, root planning, and/or occlusal adjustment is performed as known in the art. This process allows reducing a gingival inflammation so as to minimize tissue tearing during surgery and/or postsurgical healing. As known in the art, a response to such a process may be seen as a gingival tissue with a pale, firm and consistent pink color. Optionally, the patient goes through a preparation period in which she performs a plaque control treatment in order to reduce plaque as the plaque may lead to poor healing from the periodontal flap surgery and a return of periodontal defects.

Now, an immediate pre-operative procedure is performed. The patient may be prepared with a set of periodontal flap surgical instruments such as protective glasses, a surgical cap and drapes. The instruments may be laid out in specific groups in an organized manner that is optionally maintained throughout the procedure. First, the local anesthesia group is laid out, followed by a periodontal probe and explorers, and next, surgical knives and scalpels, followed by the periosteal elevators and bone chisels, together with the surgical curettes. Optionally, an ultrasonic scaler is provided, optionally with periodontal scaling instruments, such as hand scalers and the Gracey (SP) universal curettes. Optionally, a sharpening stone and a minor for the assistant are provided. Above this are the needle holder, curved hemostat, and scissors. A plastic syringe and metal bowl are used for sterile saline, and there are cotton pliers and sterile gauze. Finally, the silk suture material may be laid out.

Figure 13C:
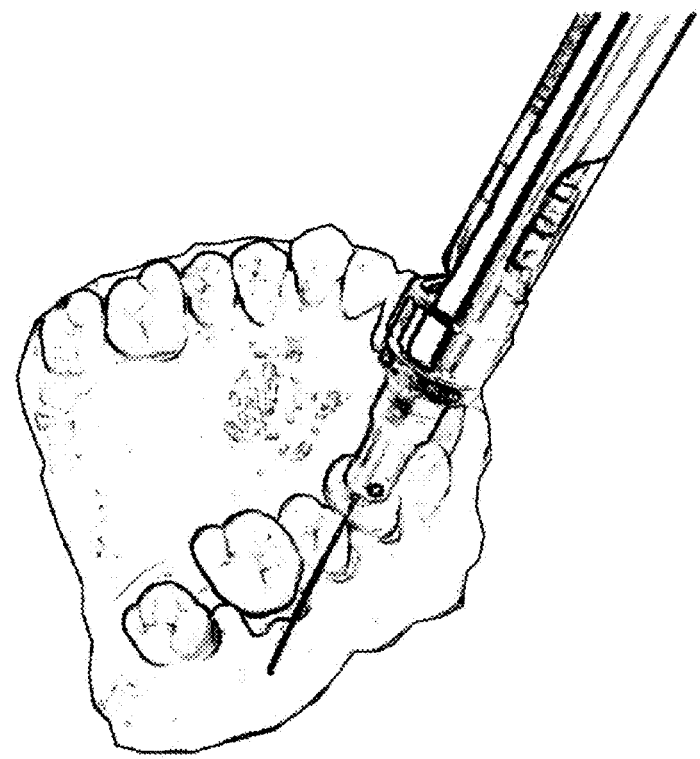

Now, as shown at 32 and depicted in FIG. 13C, anaesthetic is locally administered to the patient, preferably in a multipart process, for example as known in the art. Optionally, topical anesthesia is performed prior to injection of the anesthetics. Topical anesthetic ointment, with 20% benzocaine is applied to a cotton roll, placed in the vestibule opposite the surgical area and left in place for 2-3 minutes.

Infiltration anesthesia is used on both the buccal and lingual/palatal regions. Optionally, 2% lidocaine with 1:100, 000 concentration of vasoconstrictor is slowly injected into the buccal mucosa. The needle is slowly advanced and the patient's response in monitored so that there is minimal discomfort while the infiltration anesthesia is carried out.

When the buccal infiltration is completed, a few drops of anesthetic solution are injected into each of the interdental papillae in order to trigger vasoconstriction and some initial anesthesia on the palatal/lingual/palatal surface so as to increase comfort for the patient when the palatal infiltration anesthesia proceeds. The palatal infiltration begins in the vasoconstriction areas, near the interdental papillae so as to reduce the discomfort of the palatal injections. Palatal infiltrations progressively cover the entire area of the palatal surgery.

Now, as shown at 33, four separate palatal/lingual/palatal incisions are made, for example using a disposable scalpel blade and an interproximal knife. The first palatal/lingual/palatal incision is made with a #15 scalpel. Beginning at the distal, a scalloped, reverse bevel incision is continued anteriorally.

Figure 13D:
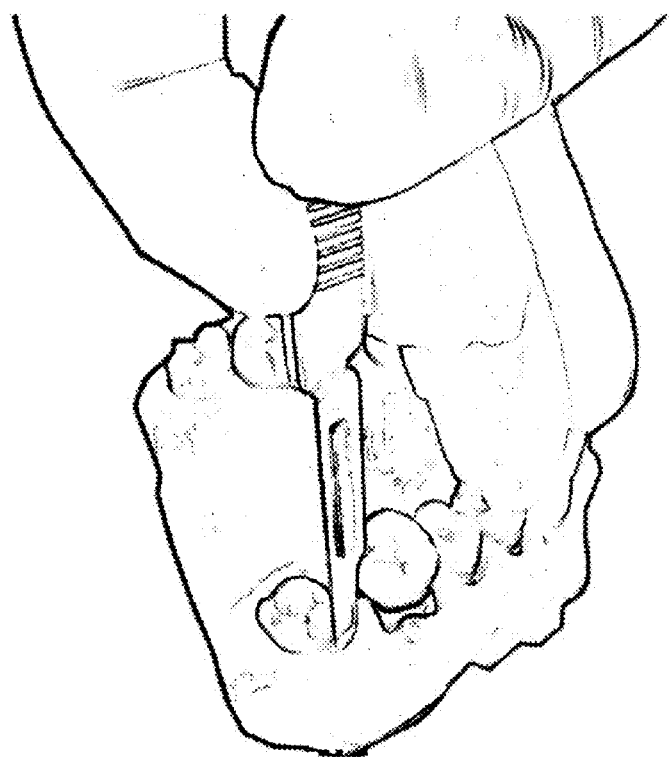

The blade is angled so that this incision is made parallel to the outer surface of the tissue, for example as shown in FIG. 13D. This insures that the flap has a thin cross-section, and so, will adapt well around the teeth. The scalloped shape is accentuated so that the incision on the surface of each tooth is more apical than the incisions in the interproximal region.

The incision is continued forward with accentuation of the scalloping of the gingival margin. A second vertical incision is placed on the mesial of the first premolar and is angled anteriorally to maximize the blood supply to the flap. The scalpel is now used to reflect the flap beginning with the vertical incision, and then a periostial elevator reflects the tissue. Complete reflection of this full thickness flap is accomplished.

In addition, preferably a release cut is made from distal to mesial on the buccal flap to enable tensionless cover of the bone implant.

Figure 13E:
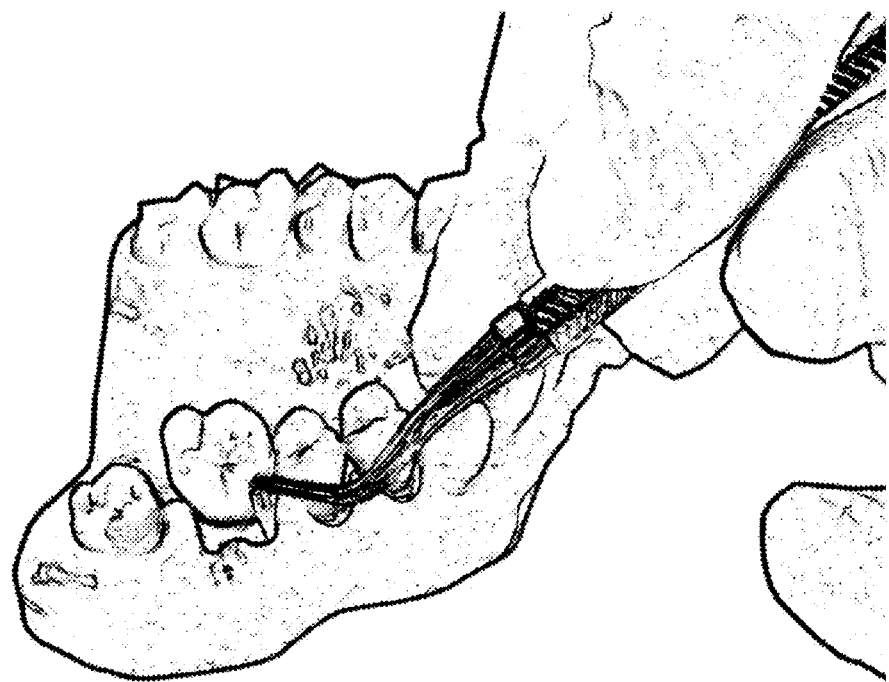
Figure 13F:
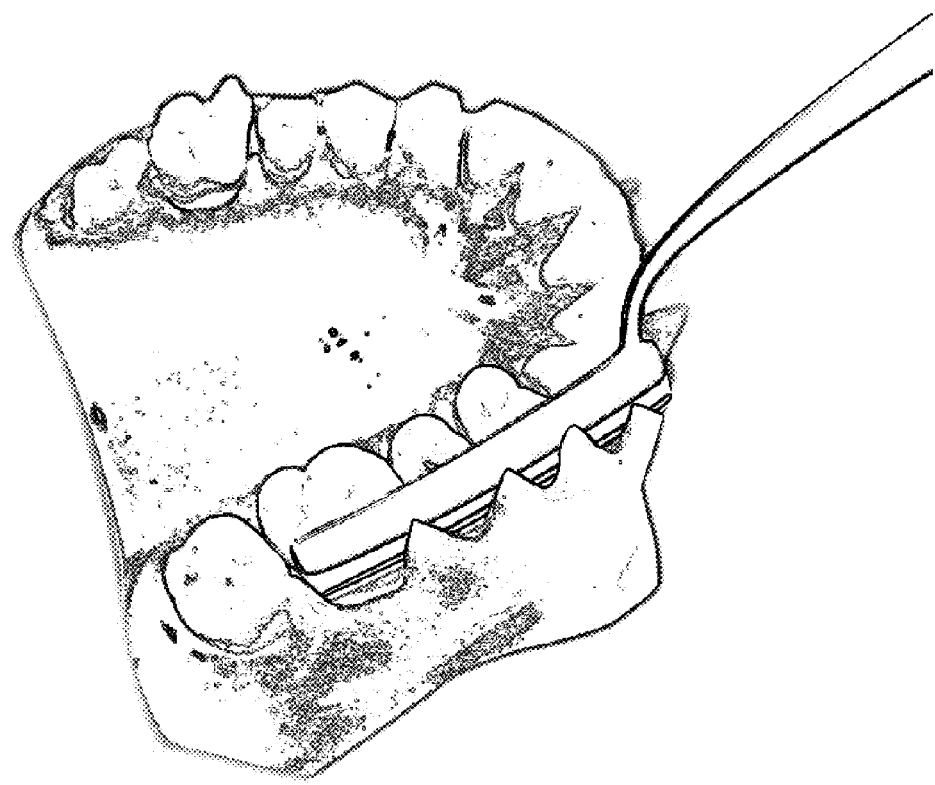

Now, as shown at 34 and depicted in FIG. 13E and/or FIG. 13F in tissues are removed and the bone margin is exposed, preferably with cleaning of the area. For example, degranulation is initiated with large dental scalers. The Ball scaler is a double-ended instrument which gives excellent interproximal access. The buccal interproximal tissues are removed in large pieces so that minimal time is taken to clean up the area and to expose the bone margin. The palatal/lingual/palatal surface is treated in the same manner. Optionally, an ultrasonic scaler is now used to remove smaller pieces of granulation tissue along the bone margins. The tip of this instrument is applied directly to the bone and clumps of tissue are removed. The instrument moves throughout the entire surgical area and will allow direct visual access of all the root surfaces. Granulation tissue removal also exposes the depths of the bony defects. The same is done on the palatal surfaces.

Optionally, Gracey curettes are used to refine the removal of the granulation tissue. All small tissue tags are removed and a clear view of the periodontal bone defects and the root surfaces is obtained.

Figure 13G:
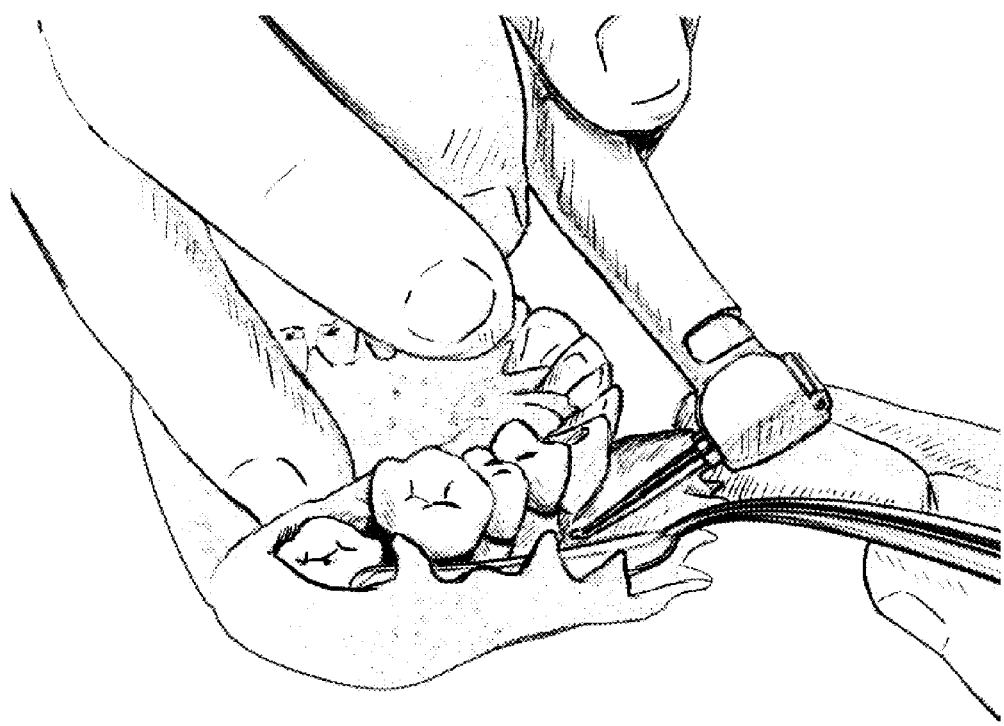

Reference is now also made to FIGS. 13A and 13B, which are schematic illustrations of retractor tools 1601, 1606 which are sized and shaped to support the gingival tissues during the implantation of the fitted bone grafts, according to some embodiments of the present invention. As shown, in FIG. 13A, the retractor tool 1601 has a left and right elongated parts, each of which features a handle 1602 and a serrated retracting portion 1604. Optionally, the serrated retracting portion 1604 is serrated on one of the edges, as shown in FIGS. 13A-13B. FIG. 13B shows a similar retractor tool 1606 in which the two pieces are joined through a common handle 1608 to which the two serrated retracting portions 1604 are attached. Similarly, the serrated retracting portion 1604 may be serrated on one edge as shown. FIGS. 13J-13L depicts how the retractor tools 1601, 1606 may be used to support the gingival tissue during the implantation. FIG. 13F depicts a reflection of the gum flaps supported with the retractor tools 1601, 1606. FIG. 13G depicts an exposure of the bone tissue with the retractor tools 1601, 1606 so as to allow a fenestration thereof.

Reference is now made, once again, to FIG. 12. As shown at 36, root planning is performed, which is one of the most important parts of periodontal surgery. Gracey curettes are first used on all accessible root surfaces. Visualization of these surfaces gives a better opportunity to obtain optimal smoothness of the roots and all visible calculus is removed. The ultrasonic scaler may be used in inaccessible surfaces such as furcations, and areas where curettes have not removed all the calculus.

Use of a slow speed handpiece with an ultrafine diamond bur may be used to smooth root surfaces that are still rough or which have calculus. Such a bur may reach into the depths of the bony crevices as well as hard-to-reach root surfaces. The root surfaces are checked with explorers, and inspected visually to be certain that no obvious calculus is left so as to clean the roots.

Figure 13H:
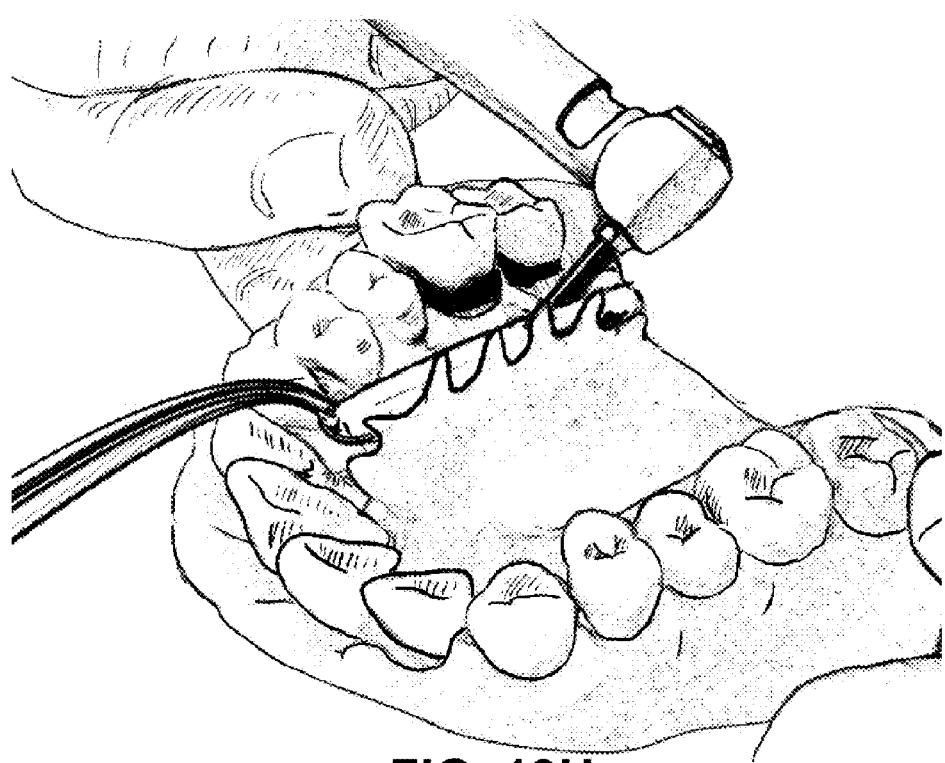

As shown at 37, one or more regenerating holes are optionally drilled into the mandible and/or the maxilla so as to perform a fenestration of the cortical plate, for example as depicted in FIGS. 13G and 13H.

Now, as shown at 38, the surgical area is washed and cleansed of any remaining debris, for example using a syringe filled with sterile saline. Optionally antibiotic agents are added to suppress the growth of maleficent microflora.

Now, as shown at 39, the root surfaces may be pretreated with one or more treatment agents, such as bone morphogenic protein, for example as depicted in FIG. 13H. The treatment agents are placed on root surfaces to enhance periodontal ligament (PDL) formation.

Figure 13I:
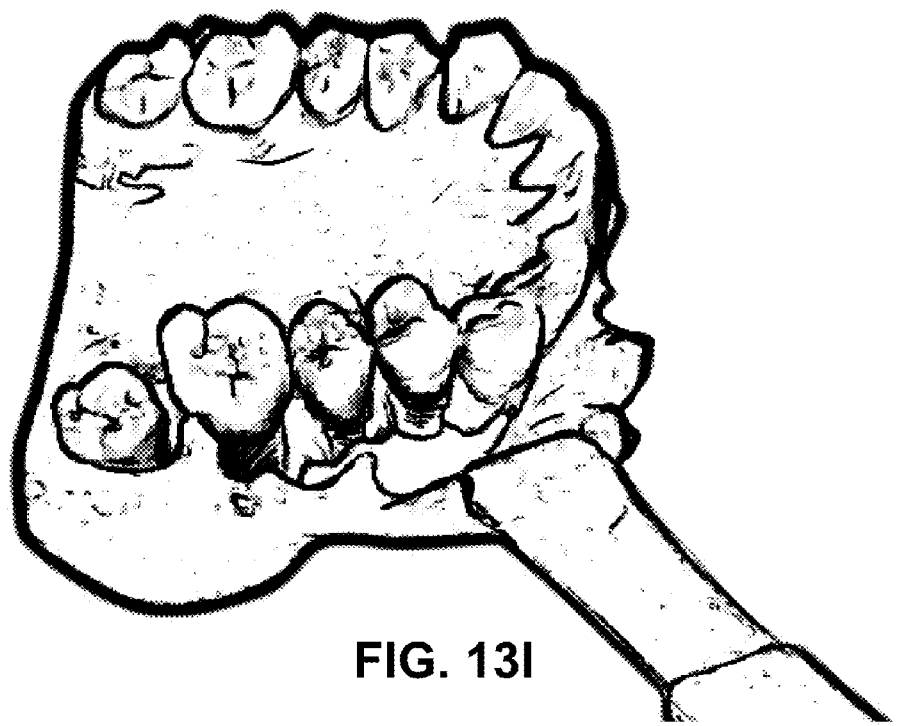
Figure 13J:
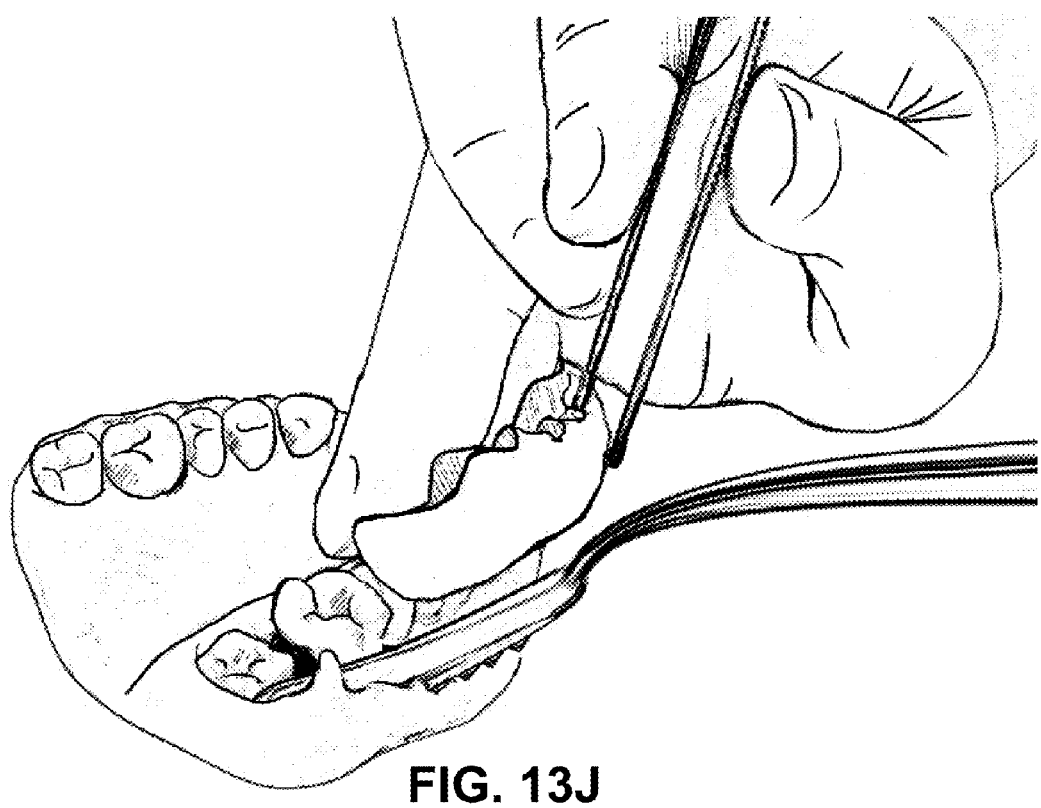
Figure 13K:
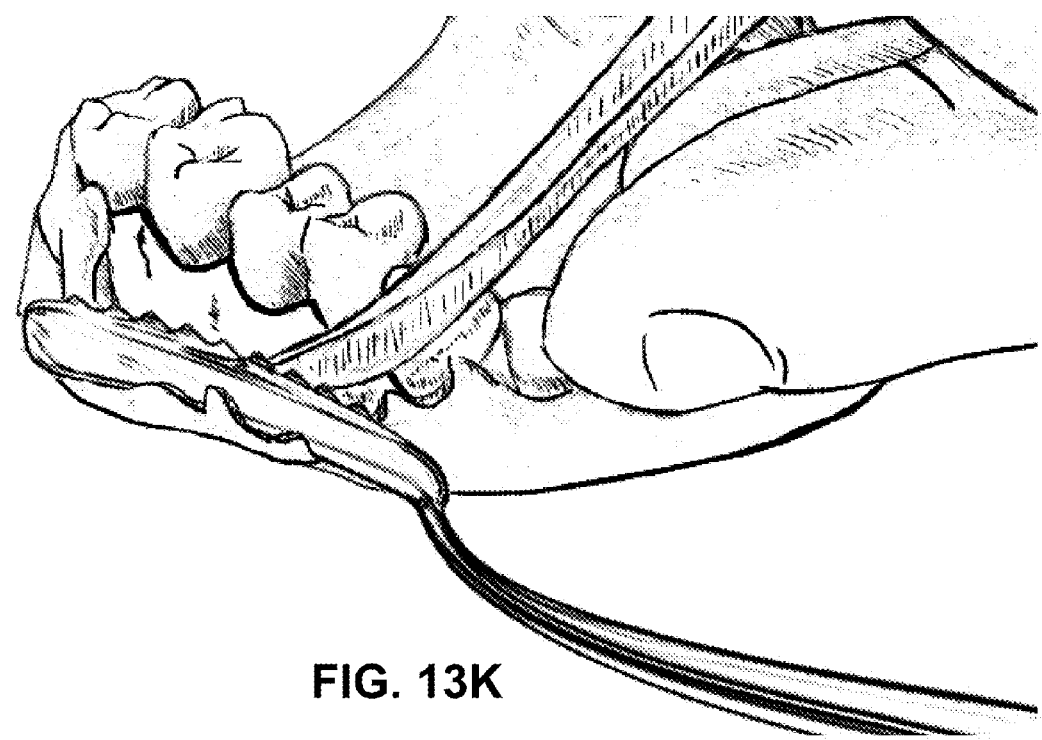
Figure 13L:
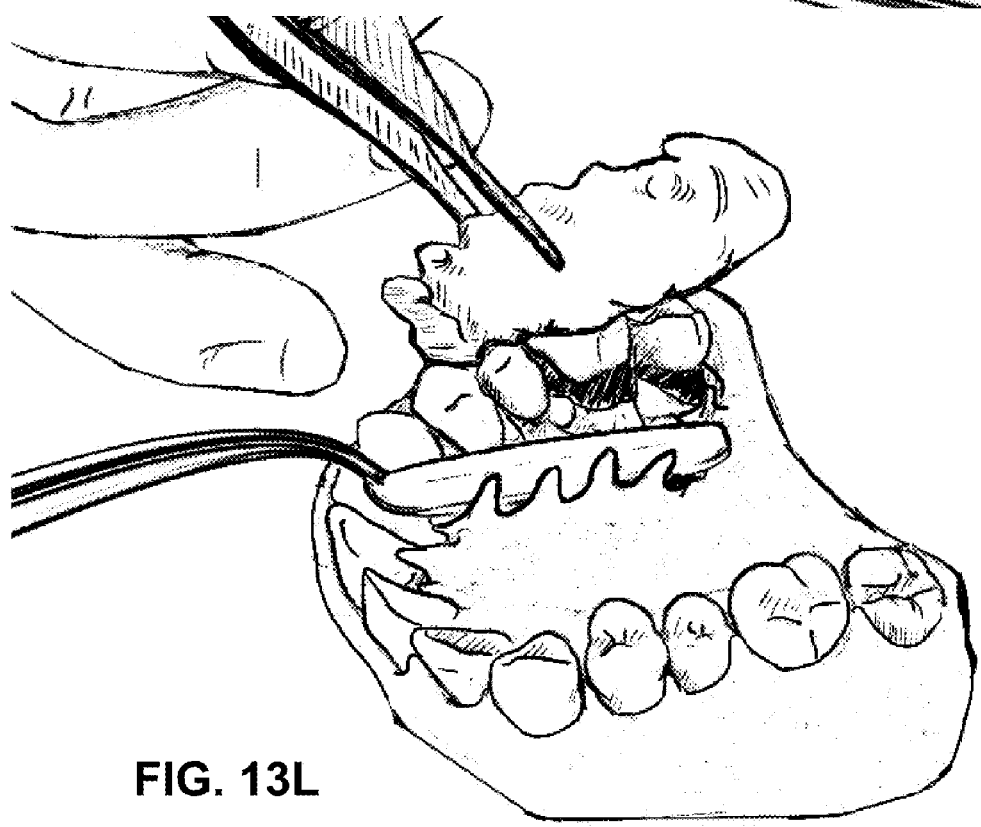

Now, as shown at 40, a dental bone implant is placed and optionally anchored by a positive seat, one or more screws, one or more fasteners, adhesives and/or any combination thereof. For example, FIG. 13I depicts an optional insertion of the bone graft on one side of the mandible, followed by insertion of the complementary bone graft on the other side of the mandible as shown in FIG. 16K.

Figure 13M:
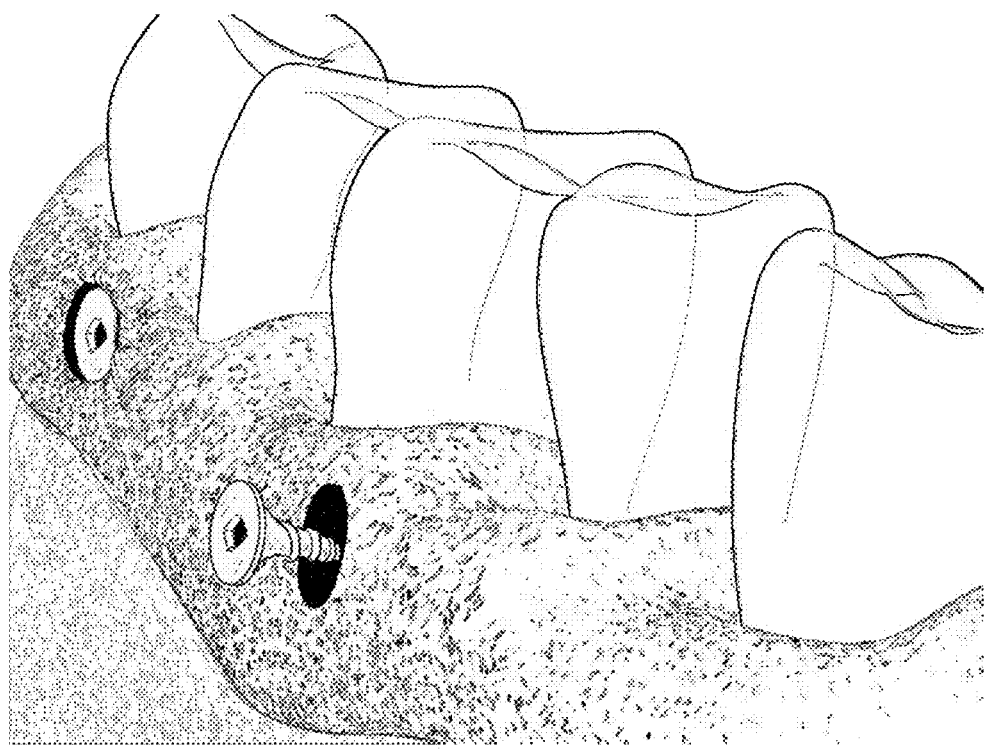
Figure 14:
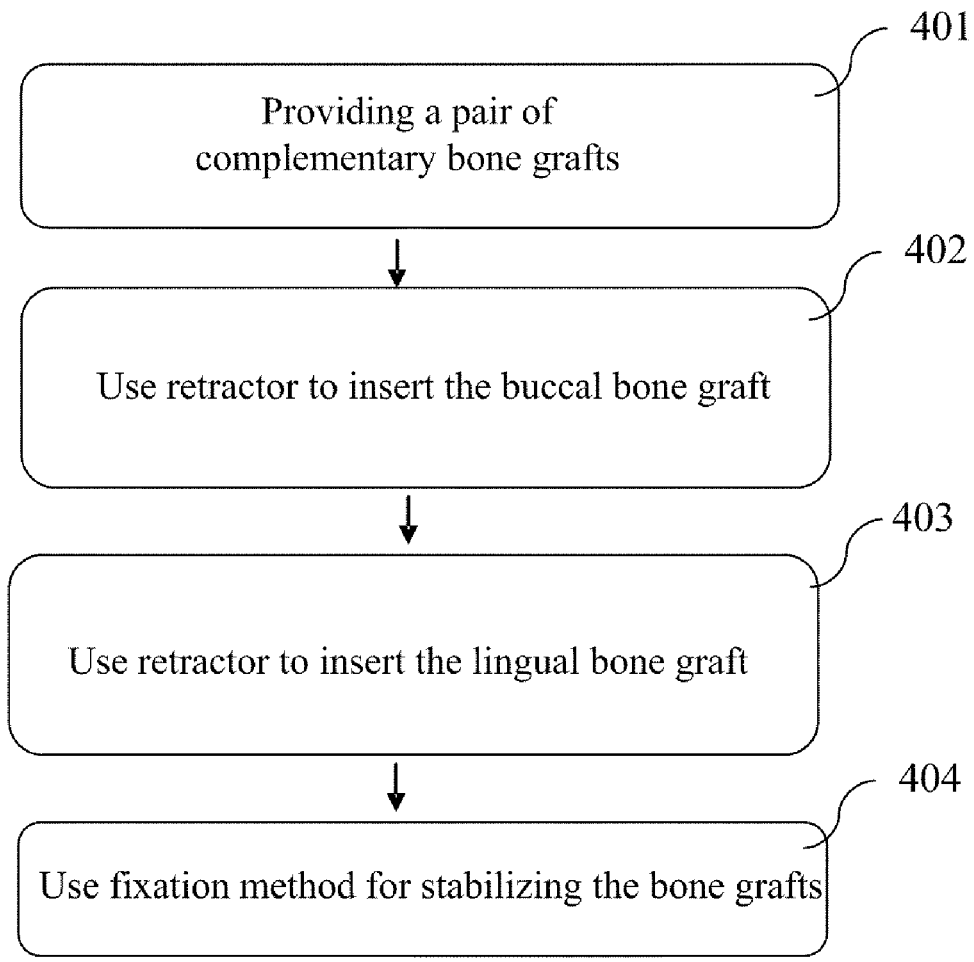
FIG. 14 is a flowchart of a process for placing and anchoring a fitted dental bone implant, according to some embodiments of the present invention.

Reference is now made to FIG. 14, which is a flowchart of a process for placing and anchoring a fitted dental bone implant, according to some embodiments of the present invention. First, a pair of complementary fitted bone grafts is provided. While one fitted bone graft is shaped to reconstruct the buccal surface of the treated periodontal alveolar bone and/or crest around one or more teeth, the other is shaped to reconstruct the lingual/palatal surface of the treated periodontal alveolar bone and/or crest around the same one or more teeth. Now, as shown at 402, a retractor and/or any other dental tool for supporting the gingival tissue is used to allow the placing of the buccal fitted bone graft between the gum and teeth, for example as shown at FIGS. 13J and 16K. As shown at 403, the retractor is also used to insert the lingual/palatal fitted bone graft between the teeth and the gum, for example as shown at FIG. 13L. Now, as shown at 404, the fitted bone grafts are anchored. Optionally, the one or more of the fitted bone grafts is screwed to the periodontal alveolar bone in the treated area for example as shown at FIG. 13M. Optionally, the surgeon drills the screwing holes according to one or more markings which are provided on the surface of the fitted bone grafts, for example as described above. Optionally, the fitted bone grafts includes one or more premade foundation elements, such as recesses and extensions, which guides the surgeon were to drill, add a dental implant and/or facilitates the anchoring of the fitted bone grafts and/or dental implants. Additionally or alternatively, the complementary fitted bone grafts are attached ton one another, for example by a screw and/or an adhesive. As described above, the fitted bone grafts are fitted to reconstruct the periodontal bone defects of the treat area on the buccal surface, the lingual/palatal surface, and/or the surface between the teeth of the mandible or the maxilla. When placed on the treated area, for example as described above, the fitted bone graft fills niches and fractures of periodontal bone defects, allowing a consolidation of the fitted bone graft with the surface of the treated area. Furthermore, the fitted bone graft increases the surface area of hard tissues which encircle the teeth in the treated area. In such a manner, fitted bone grafts reconstruct the support of the existing teeth in the treated area, function as a scaffold for cell bone regeneration, and/or support added dental implants, optionally permanently. It should be noted that as the fitted bone graft is fitted to the surface of the treated area the bone augmentation process, also known as fusing, is accelerated.

Reference is now made, once again, to FIG. 12. As shown at 41, after the fitted bone grafts are placed and optionally anchored, the cut gingival tissues are reattached above the fitted bone grafts, optionally by suturing. Optionally, before the reattachment, the bone surface is treated to enhance implantation, for example as shown at FIG. 13K. The treatment may include adding osteoinductive materials, such as hydroxyapatite, PepGen P-15™, proteins or bone morphogenetic proteins to promote bone formation.

Figure 13N:
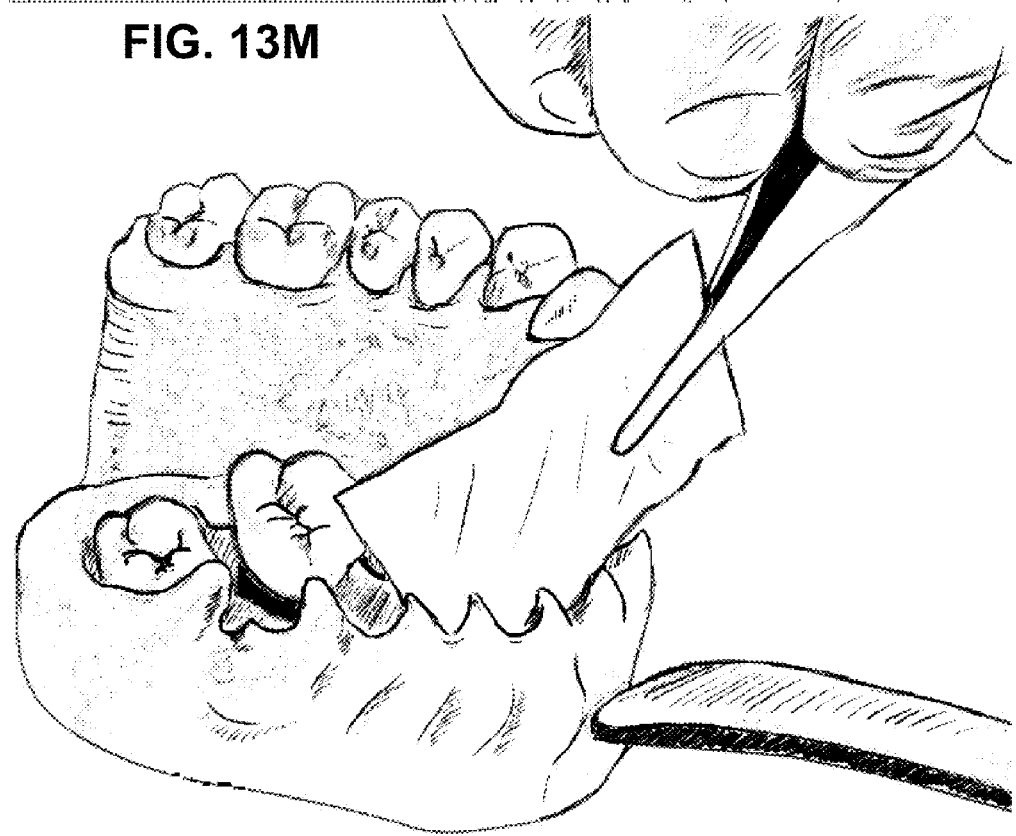
Figure 13O:
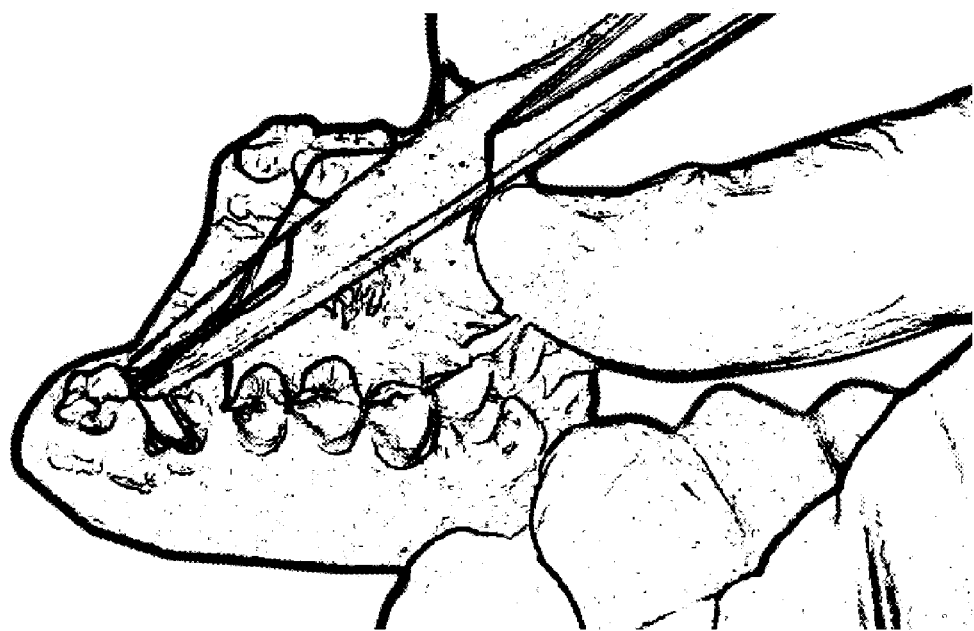
Figure 13P:
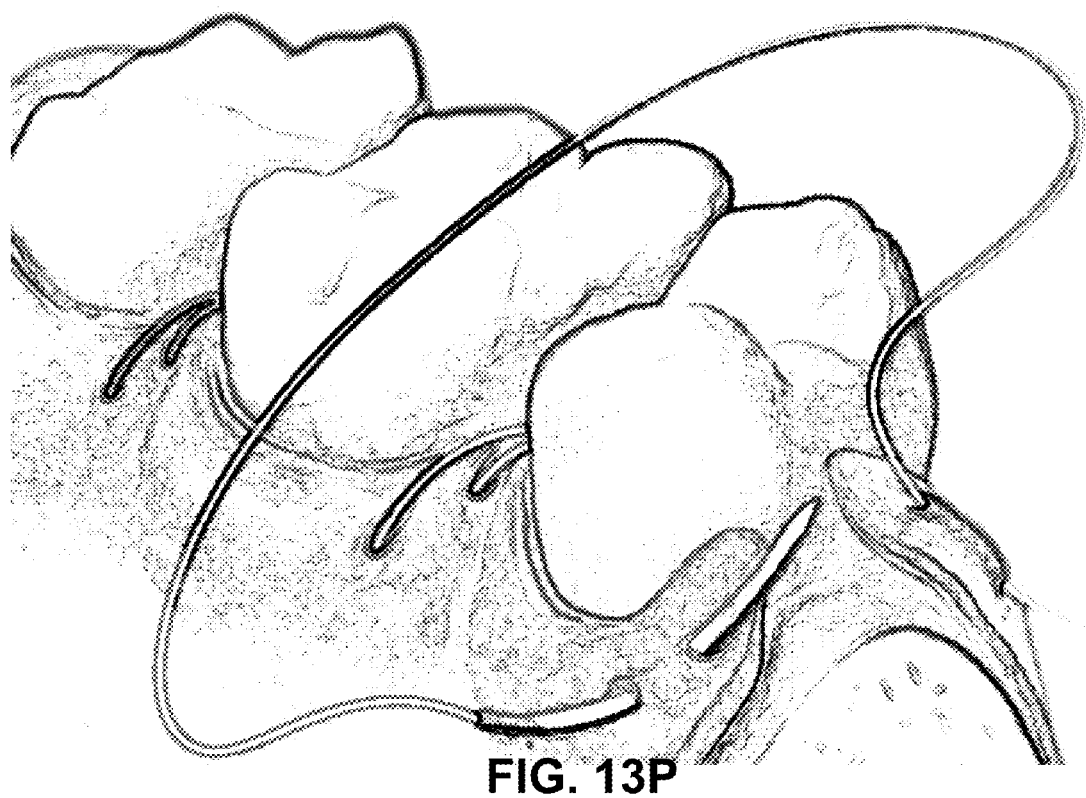

Additionally or alternatively, before the reattachment, the bone grafts are covered with a layer of barrier membrane, for example as shown in FIG. 13N which depicts the insertion of the barrier membrane and the installation thereof on one or more of the bone grafts, the barrier membrane in one embodiment inserted with tweezers as illustrated in FIG. 13N.

Figure 15A:
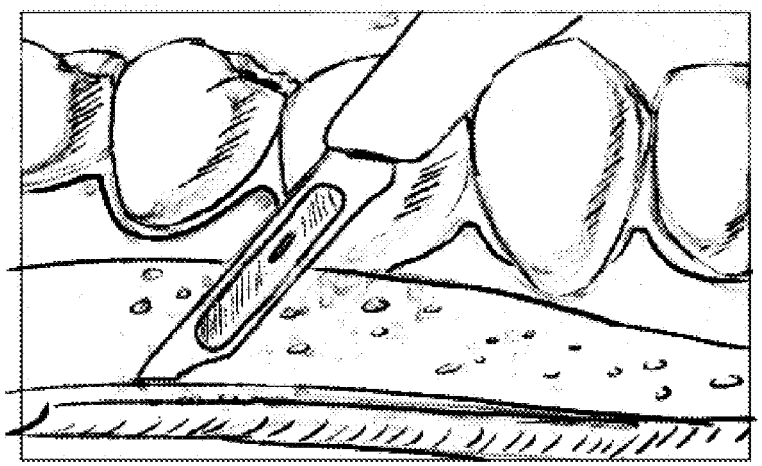
FIGS. 15A-15C are pictorial illustrations of a process for placing a gingival tissue growth promoting membrane on a fitted bone graft, according to some embodiments of the present invention.
Figure 15B:
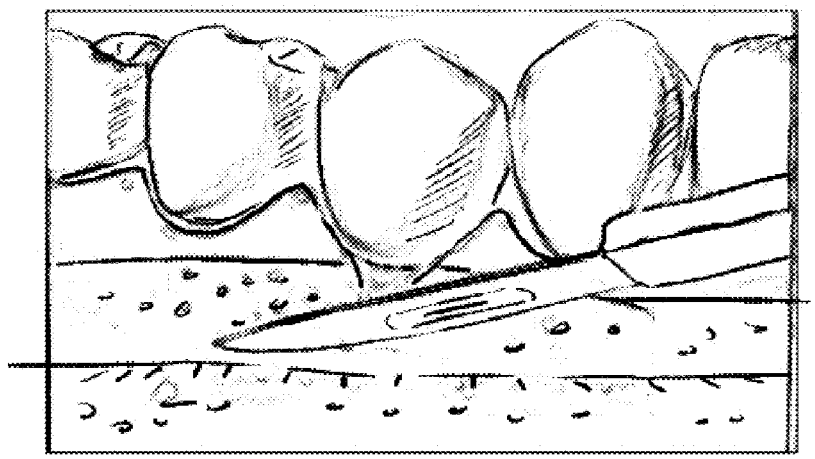
Figure 15C:
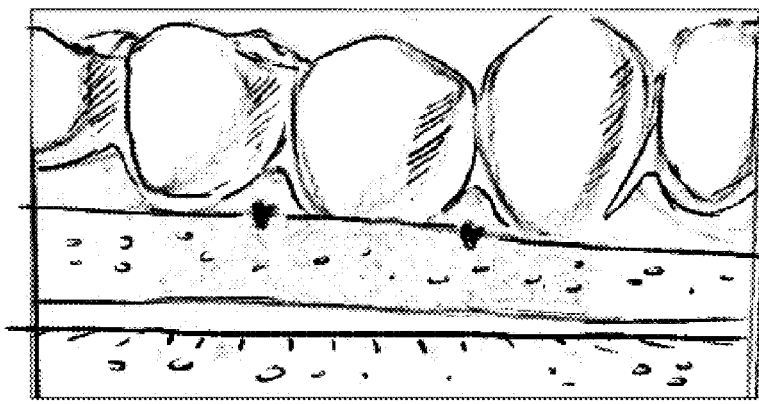

Additionally or alternatively, before the reattachment, the bone grafts are covered with a layer of gingival tissue growth promoting membrane, for example as shown in FIGS. 15A-15C which depict an optionally process for adding such a membrane after the dental bone implant is anchored in the treated area, for example to the periodontal alveolar bone. The gingival tissue growth promoting membrane assists the gingival tissue to grow and cover the bone grafts. Gingival tissue growth promoting membranes are optionally placed along the length of the buccal and/or lingual/palatal surfaces of the mandible or the maxilla, above the bone grafts and the gum so as to seal the gum against the teeth and bone grafts. As shown, in FIG. 15A incision is made to anchor the membrane in the gum. In FIG. 15B, the membrane is placed in the incision and against the gum. In FIG. 15C, the membrane is sealed against the gum.

Optionally, the tensionless flap suturing begins from the distal portion forward with a simple sling suture with anchors placed around the tooth to hold the tissue at the correct position. Care should be taken to position the flap close to the bone margin and to get the best possible flap adaption interproximally. The needle penetrates each papilla in keratinized tissue, optionally 3-4 mm away from the flap margin. Each interproximal tissue is positioned and the continuous suture moves forward. The two flaps are tied with a knot in the anterior portion of the surgery, for example as shown at FIG. 13P.

Now, as shown at 42, pressure is applied to the flaps for 2-3 minutes to promote close flap adaption and hemostasis, for example using gauze moistened with saline.

As shown at 43, the treated area is cleaned, sterilized, and optionally covered, for example using a surgical dressing. The dressing protects the treated area from mechanical trauma. Optionally, the surgical dressing is mixed and placed in sterile saline. When the dressing is set enough not to stick to the gloves, a roll is applied to the palatal, and then another roll is applied to the buccal. The dressing is pushed interproximally. Cotton pliers are used to lock the dressing in the embrasures. This joins the buccal and palatal rolls. The area may now be checked to assure there is no excess dressing in the vestibule and on the occlusal surface.

Now, as shown at 44, post operational procedures may be practiced by the patient. For example, during approximately a week after the implantation the patient may take analgesic tablets and does not brush and/or floss the area of the dressing. In addition, after a suitable period of time, for example about two weeks, the dressing is gently removed and the treated area is lightly cleansed, for example with saline, and the sutures are removed. The patient may be follow oral hygiene instructions and monitored, optionally after one week.

The process described in blocks 31 to 44 may be repeated to a number of complementary fitted bone grafts, for example 1, 2, 3, and 4. For example, numeral 902 in FIG. 8C depicts two pairs of fitted bone grafts which are fitted to reconstruct periodontal bone defects in the left and right sides of the mandible.

Optionally, one or more pairs of complementary fitted bone grafts may be implanted to reconstruct treated area around the maxillary left teeth, namely some or all of the central incisor, lateral incisor, canine, first premolar, second premolar, first molar, second molar, and third molar in the maxillary left portion of the jaws. Additionally or alternatively, one or more pairs of complementary fitted bone grafts may be implanted to reconstruct treated area around the maxillary right teeth, namely some or all of the central incisor, lateral incisor, right canine, first premolar, second premolar, first molar, second molar, and third molar in the maxillary right portion of the jaws. Additionally or alternatively, one or more pairs of complementary fitted bone grafts may be implanted to reconstruct treated area around the mandibular left teeth, namely some or all of the central incisor, lateral incisor, right canine, first premolar, second premolar, first molar, second molar, and third molar in the mandibular left portion of the jaws. Additionally or alternatively, one or more pairs of complementary fitted bone grafts may be implanted to reconstruct treated area around the mandibular right teeth, namely some or all of the central incisor, lateral incisor, right canine, first premolar, second premolar, first molar, second molar, and third molar in the mandibular right portion of the jaws.

According to some embodiments of the present invention, a fitted bone graft is placed to reconstruct an edentulous area of the mandible and/or the maxilla of the patient. In such an embodiment, as described above, there is not need to use a complementary fitted bone grafts as there is no need to encircle the teeth. In such an embodiment, blocks 31-39 and 41-44 are applied similarly to the described above, mutatis mutandis. Block 40, on the other hand, is executed differently. Optionally, instead of two complementary fitted bone grafts only one or more single fitted bone graft are placed on the treated area. The one or more single fitted bone grafts are fitted to reconstruct both the buccal and the lingual/palatal surfaces of the treated area. Optionally, a single fitted bone graft is used, for example as shown at FIG. 9E. Optionally, the retractor is used to support the gingival tissues from both sites of the treated area. Then, after the bone graph placed above the treated area it is anchored similarly to the described above.

Additionally or alternatively, one or more tooth implants are attached to one or more of the fitted bone grafts. The tooth implants may be attached to the fitted bone grafts in advance, during, and/or after the procedure. Optionally, the fitted bone grafts are provided with one or more foundation elements that function as tooth sockets or support to the tooth implants.

The procedure is generally similar, including preparation, anesthesia, flap reflection, release cut, implant placing and tensionless suturing.

Figure 16:
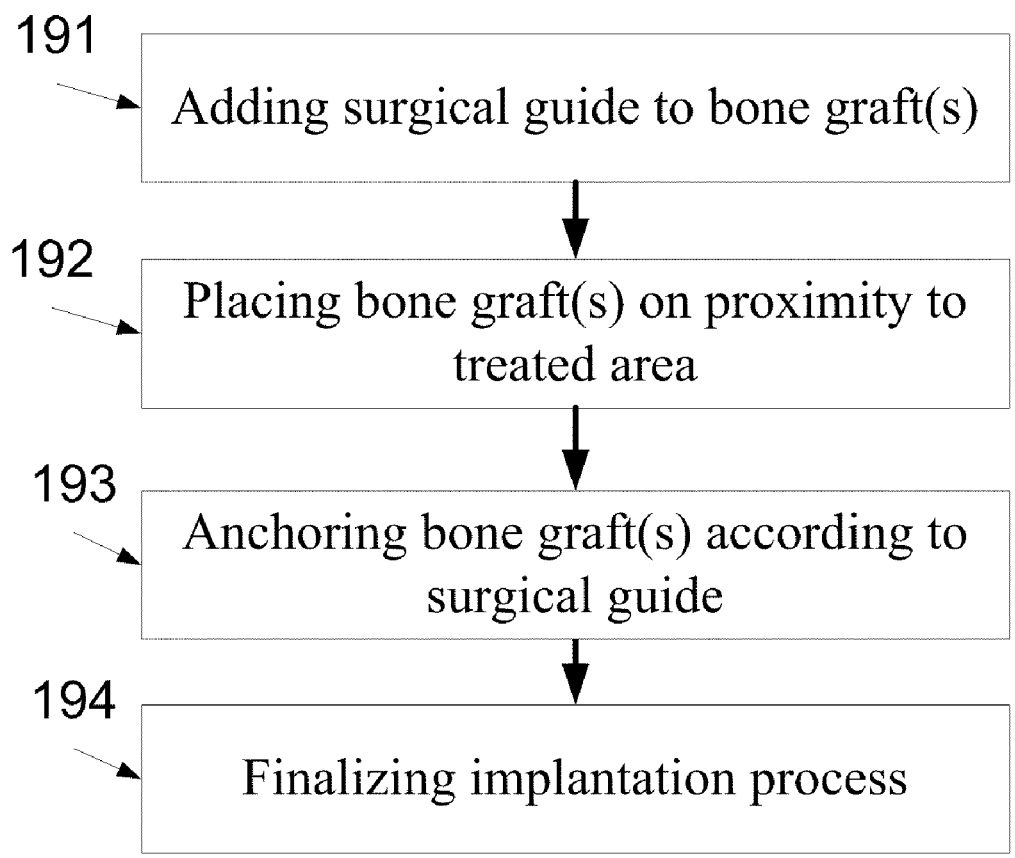
FIG. 16 is a flowchart of a method for implanting bone grafts having surgical guide elements, according to some embodiments of the present invention.

Reference is now also made to FIG. 16, which is a flowchart of a method for implanting one or more bone grafts having surgical guide elements, according to some embodiments of the present invention. First, as shown at 191, surgical guide elements are added to one or more bone grafts. Optionally, the surgical guide elements are added during a dental bone implant generation process, for example according to a dental bone model and/or sub models, for example as described above. In such an embodiment, surgical guide elements which are defined in the model are added to the bone graft during the generation thereof. Optionally, the surgical guide is added to the one or more bone grafts according to one or more characteristics of a designated treated area, for example its surface, pathology, and/or any other anatomical and/or clinical data pertaining to the patient. Optionally, the surgical guide is adjusted according to the raw material of the each respective bone graft. Optionally, the surgical guide elements are markings, foundation elements such as recesses and bores, and/or any surgical indication. Optionally, each surgical guide element indicates a drilling location, a drilling depth, and/or a drilling diameter. Now, the one or more bone grafts are placed on or in proximity to a treated area having periodontal alveolar bone and/or crest defects, for example as shown at 192, and similarly to the described above in relation to blocks 31-39 of FIG. 12. Now, as shown at 193, the surgeon anchors the one or more bone grafts according to the surgical guide. For example, the surgeon fastens screws according to drilling markings and/or preprocessed recesses and/or bore. Now, as shown at 194, the surgeon finalizes the implementation process, for example as depicted in blocks 41-44 of FIG. 12.

It is expected that during the life of a patent maturing from this application many relevant systems and methods will be developed and the scope of the term fitted bone graft, raw materials, regenerative agents, and osteogenetic material is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A dental bone implant, comprising:
    a first fitted bone graft sized and shaped to fit tightly to a buccal surface of a periodontal alveolar bone around at least one native tooth and to reconstruct at least a portion of at least one periodontal bone defect; and
    a second fitted bone graft, different from said first fitted bone graft, sized and shaped to fit tightly to a lingual/palatal surface of a periodontal alveolar bone around the at least one native tooth and to reconstruct at least an additional portion of the at least one periodontal bone defect;
    wherein said portion and said additional portion complementary cover said at least one periodontal bone, and
    wherein said first fitted bone graft and said second fitted bone graft complementary surround the at least one native tooth.

2. The dental bone implant of claim 1, wherein said first fitted bone graft comprises a first extension sized and shaped to reconstruct completely a first tooth socket and said second fitted bone graft comprises a second extension sized and shaped to reconstruct completely a second tooth socket, different from the first tooth socket.

3. The dental bone implant of claim 2, wherein said first and second tooth socket are placed on different sides of the at least one native tooth.

4. The dental bone implant of claim 1, wherein at least one of said first and second fitted bone grafts is configured to be implanted on top of said periodontal alveolar bone until being entirely replaced by native bone originated from a growth of said periodontal alveolar bone.

5. The dental bone implant of claim 1, wherein said at least one tooth comprises a plurality of teeth, wherein at least one of said first and second fitted bone grafts being sized and shaped to fit tightly to an interdental surface between said plurality of teeth.

6. The dental bone implant of claim 1, wherein at least one of said first and second fitted bone grafts comprises a structure defined by a three dimensional model of said periodontal alveolar bone.

7. The dental bone implant of claim 1, wherein at least one of said first and second fitted bone grafts is at least partly coated with a barrier membrane.

8. The dental bone implant of claim 1, wherein at least one of said first and second fitted bone grafts is sized and shaped to reconstruct at least one teeth socket.

9. The dental bone implant of claim 1, wherein at least one of said first and second fitted bone grafts comprises a periodontal regenerative agent.

10. The dental bone implant of claim 9, wherein said periodontal regenerative agent is selected from a group consisting of promoting regeneration agent and limiting regeneration agent.

11. The dental bone implant of claim 1, wherein at least one of said first and second fitted bone grafts is shaped for vertical augmentation.

12. A dental bone implant, comprising:
    a first fitted bone graft sized and shaped to fit tightly to at least one of buccal and lingual/palatal surfaces of a periodontal alveolar bone around at least one native tooth and to reconstruct at least a portion of at least one periodontal bone defect; and
    a second fitted bone graft, different from said first fitted bone graft, sized and shaped to fit tightly to at least one of buccal and lingual/palatal surfaces of a periodontal alveolar bone around the at least one native tooth and to reconstruct at least an additional portion of the at least one periodontal bone defect,
    wherein said first fitted bone graft and said second fitted bone graft complementary surround the at least one native tooth, and
    wherein said first fitted bone graft is configured to be anchored between said periodontal alveolar bone and a gingival tissue of a patient for a period of at least one week.

13. The dental bone implant of claim 12, wherein said first fitted bone graft is sized and shaped to fit tightly to a buccal surface of the periodontal alveolar bone around the at least one native tooth, and
    wherein said second fitted bone graft is sized and shaped to fit tightly to a lingual/palatal surface of the periodontal alveolar bone around the at least one native tooth.

14. The dental bone implant of claim 12, wherein said portion and said additional portion complementary cover said at least one periodontal bone.

15. The dental bone implant of claim 12, wherein said first fitted bone graft comprises an extension sized and shaped to reconstruct completely a first tooth socket in proximity to the at least one native tooth and said second fitted bone graft comprises a second extension sized and shaped to reconstruct completely a second tooth socket in proximity to the at least one native tooth, the second tooth socket different from the first tooth socket.

* * * * *